(12) United States Patent
Kenny et al.

(10) Patent No.: US 6,677,576 B1
(45) Date of Patent: Jan. 13, 2004

(54) FIBEROPTIC COUPLER SENSOR AND A MEASUREMENT METHOD

(75) Inventors: Robert P. Kenny, Ispra (IT); Maurice P. Whelan, Ispra (IT); Alfredo C. Lucia, Ispra (IT); Conleth D. Hussey, Limerick (IE); Paul F. O'Sullivan, Limerick (IE); Elaine M. O'Brien, Limerick (IE)

(73) Assignee: European Community represented by Commission of the European Communities, Luxembourg (LU)

( * ) Notice: Subject to any disclaimer, the term of this patent is extended or adjusted under 35 U.S.C. 154(b) by 0 days.

(21) Appl. No.: 09/787,523

(22) PCT Filed: Sep. 20, 1999

(86) PCT No.: PCT/GB99/03124
§ 371 (c)(1),
(2), (4) Date: May 11, 2001

(87) PCT Pub. No.: WO00/17608
PCT Pub. Date: Mar. 30, 2000

(30) Foreign Application Priority Data

Sep. 18, 1998 (GB) ............................................... 9820467

(51) Int. Cl.$^7$ .................................................. G01J 1/04
(52) U.S. Cl. ........................... 250/227.14; 250/227.16; 356/73.1; 385/12
(58) Field of Search ....................... 250/227.14, 227.11, 250/216, 227.16, 340, 385; 356/28–29, 32, 35, 73.1; 385/12–13, 43, 50, 123, 136, 7–8, 16, 95–96; 73/488, 653, 705, 861.08, 861.18, 204.11; 340/555–557

(56) References Cited

U.S. PATENT DOCUMENTS 5,026,984 A  *  6/1991  Gerdt ..................... 250/227.21
5,078,465 A  *  1/1992  Dahlgren ...................... 385/50
5,222,165 A  *  6/1993  Bohlinger ..................... 385/16
5,258,614 A  * 11/1993  Kidwell et al. ......... 250/227.16
6,463,187 B1 * 10/2002  Baruch et al. ................ 385/12

FOREIGN PATENT DOCUMENTS

| EP | 0 178 806 | 4/1986 |
| GB | 2 197 946 | 6/1988 |
| JP | 010129127 | 5/1989 |
| JP | 07 159255 | 6/1995 |
| WO | WO 94/16346 | 1/1993 |

OTHER PUBLICATIONS

"Miniature High Performance Loop Reflector", Oakley et al., Electronics Letters Dec. 5, 1991, vol. 27 No. 25, pp. 2334–2335.

* cited by examiner

Primary Examiner—David Porta
Assistant Examiner—Patrick J. Lee
(74) Attorney, Agent, or Firm—Westman, Champlin & Kelly, P.A.

(57) ABSTRACT

Sensors and sensing apparatus are described, based on fused tapered fiber optic couplers with the taper waist portion formed into a loop or cleaved to provide a reflecting end. Light is typically input to the taper waist portion along a single input fiber, and bending of the loop or cleaved taper waist portion causes changes in the coupling ratio between the output fibers. The taper waist portion may be formed into a loop with a small bend radius without loss, and sensors embodying the claimed invention are particularly suitable for in-vivo measurement of pressure, the taper waist portions advantageously being arranged in contact with a membrane which deflects according to surrounding pressure. Further embodiments are described which are suitable for measurement of fluid flow velocity and/or acceleration.

50 Claims, 10 Drawing Sheets

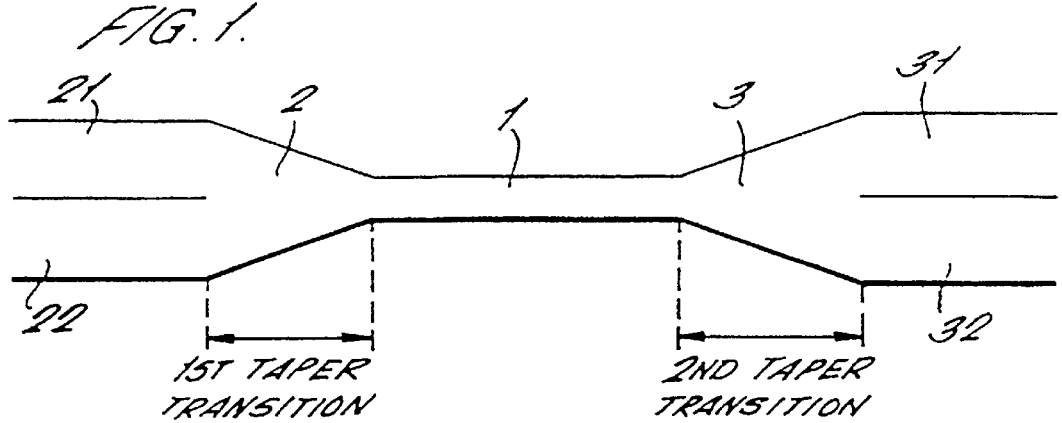
FIG. 1.
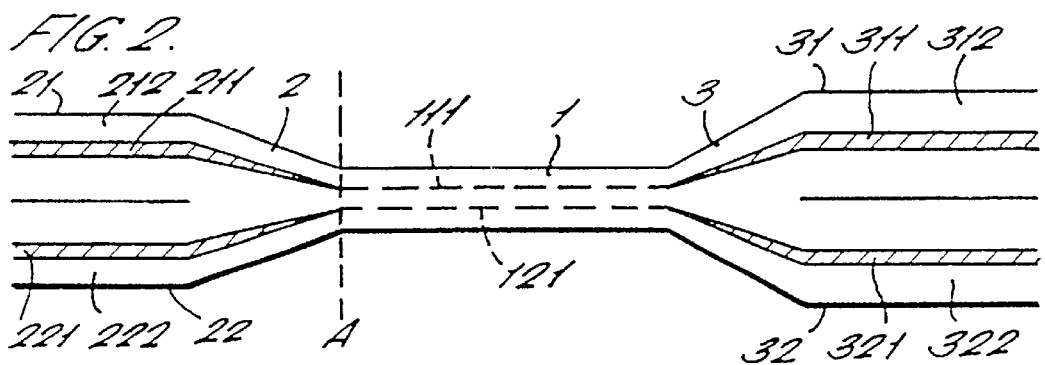
FIG. 2.
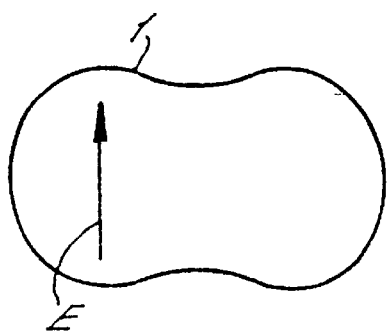
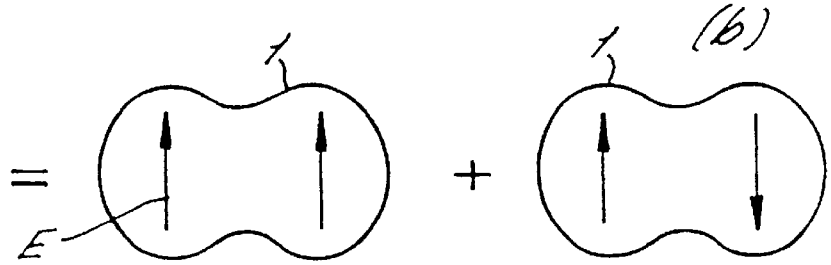
FIG. 3.

FIG. 8.
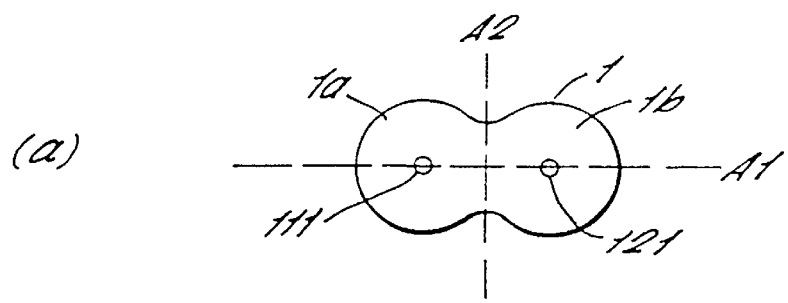
(a)
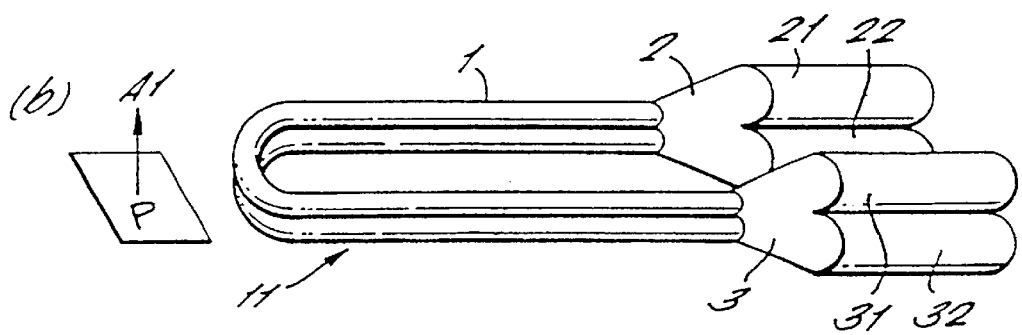
(b)
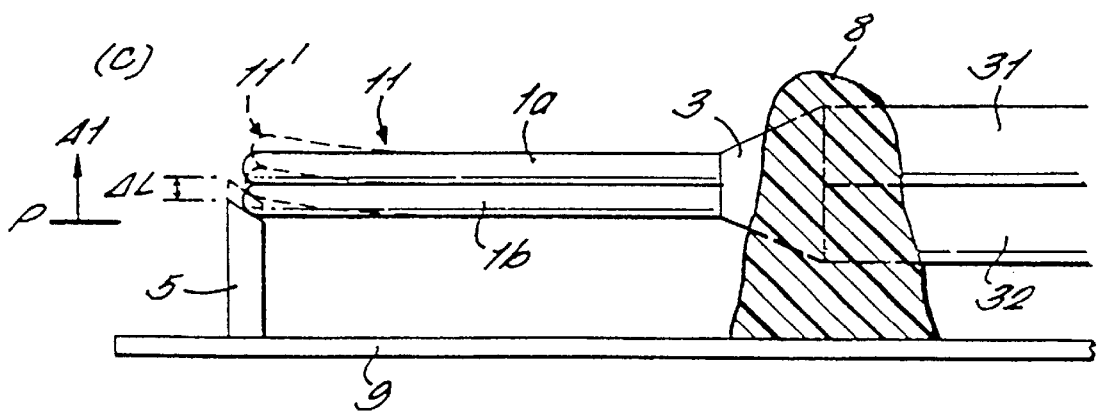
(c)

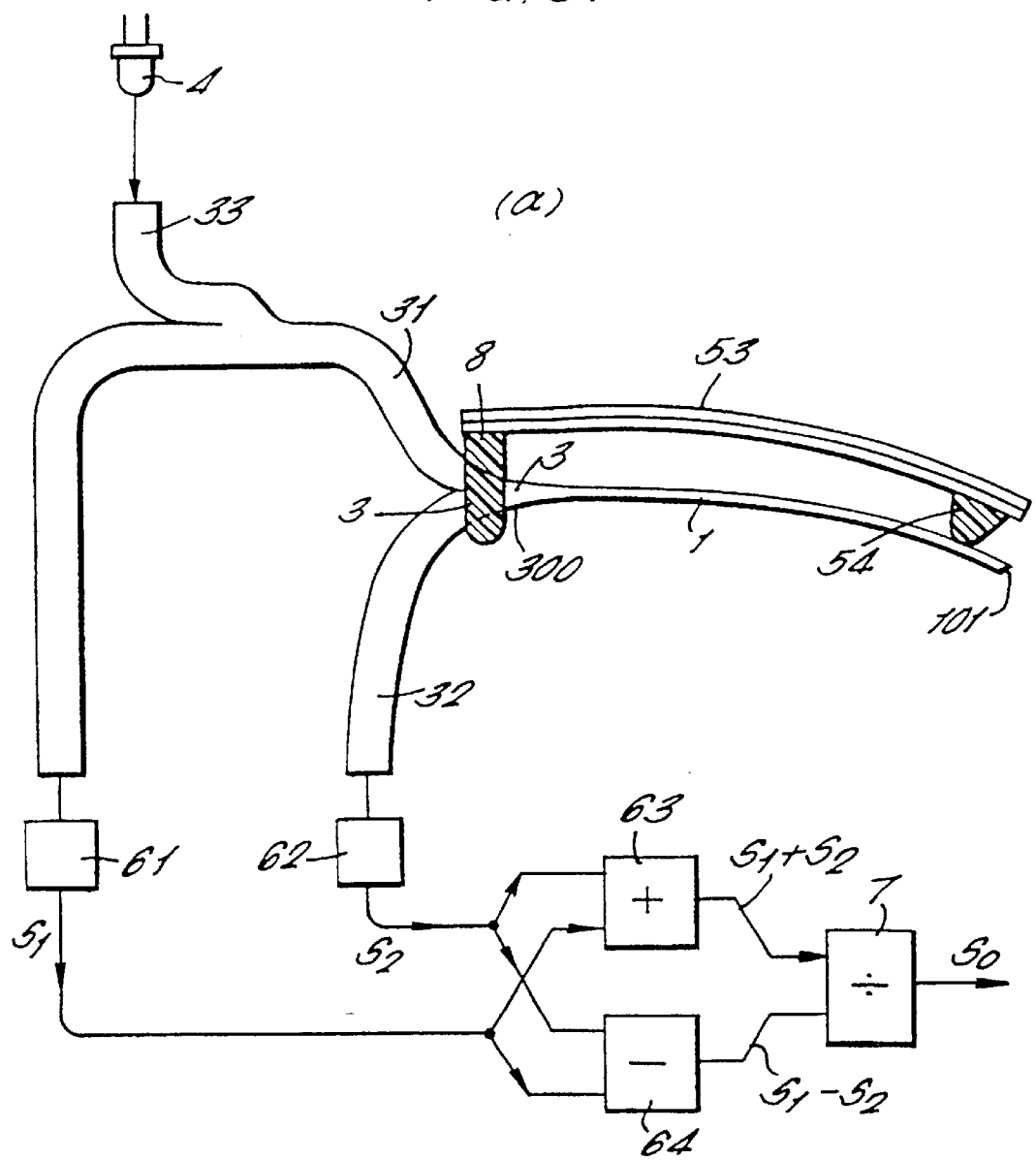
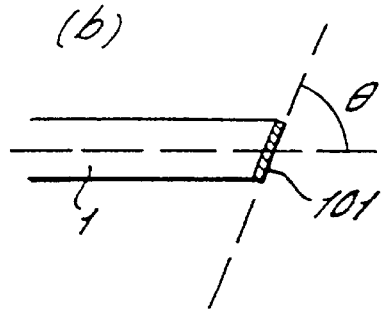
FIG. 9.

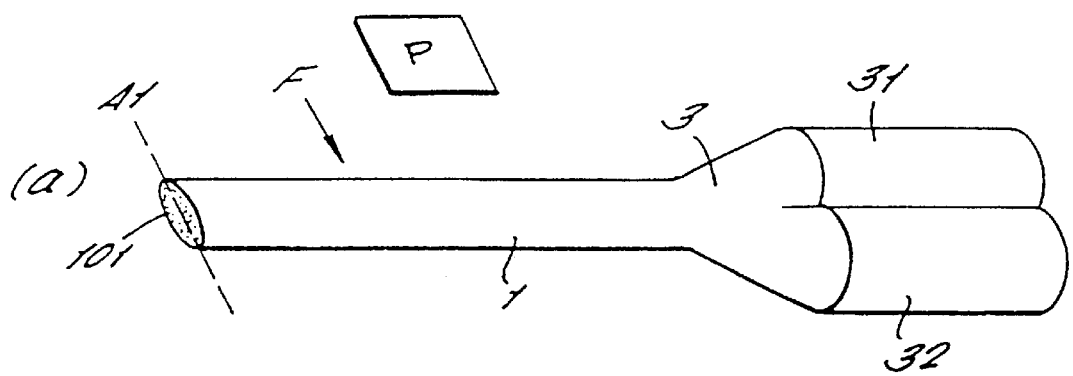
FIG. 10.
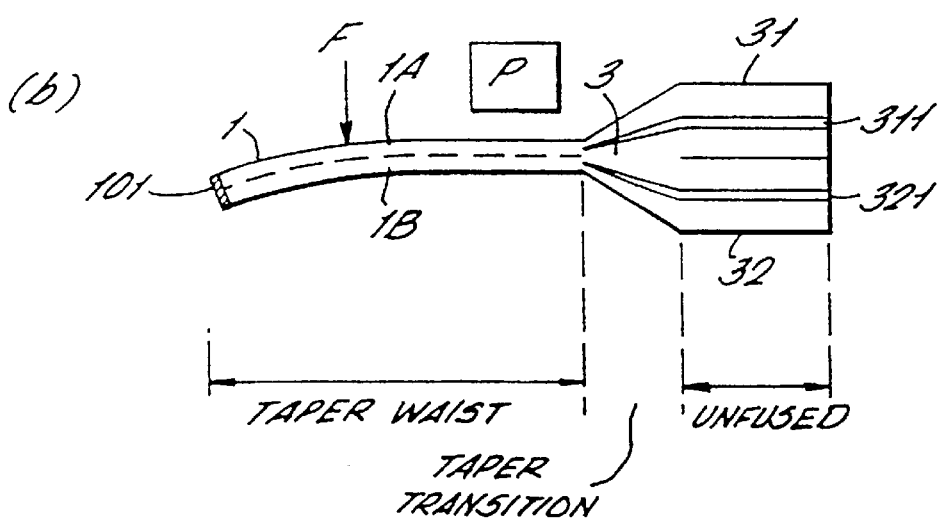
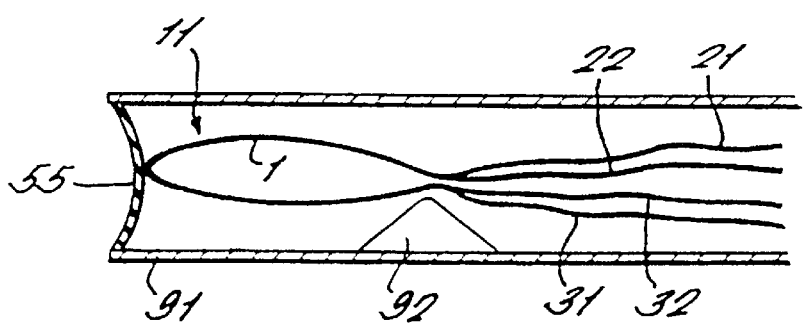
FIG. 11.

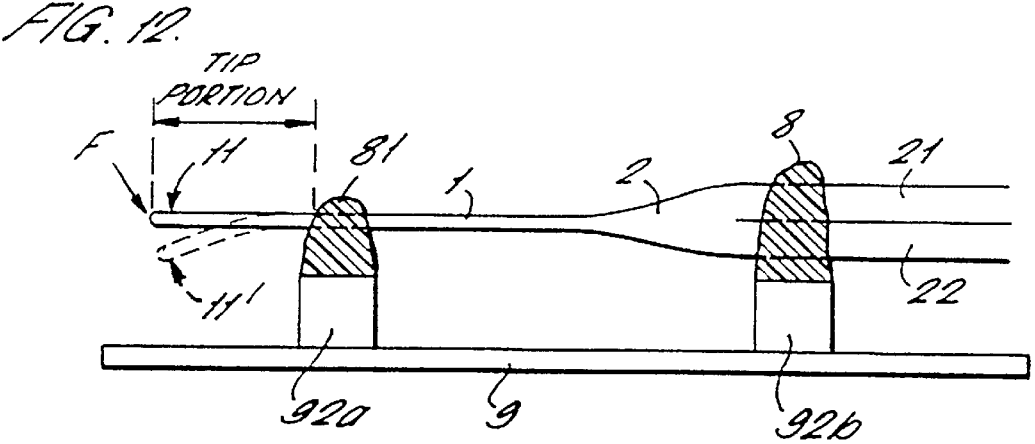
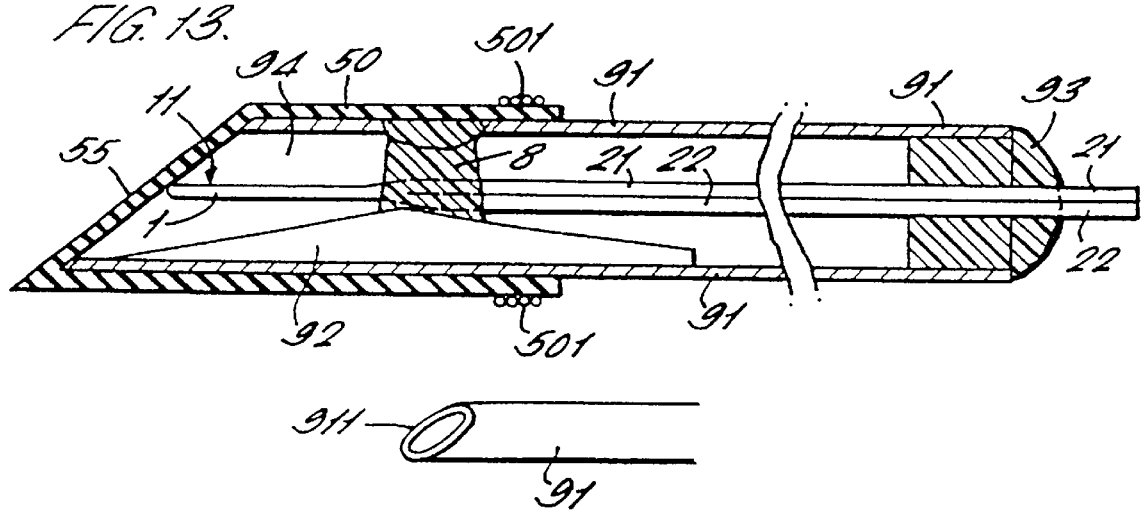
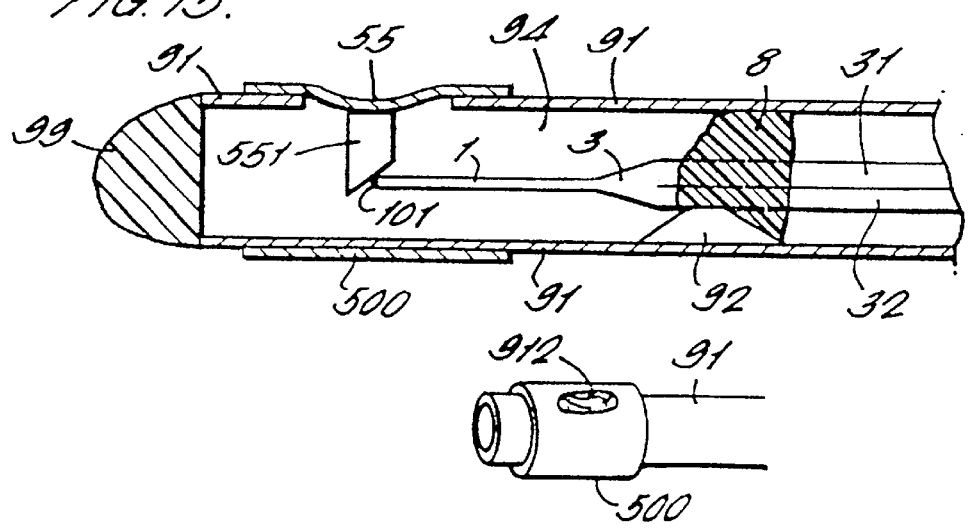

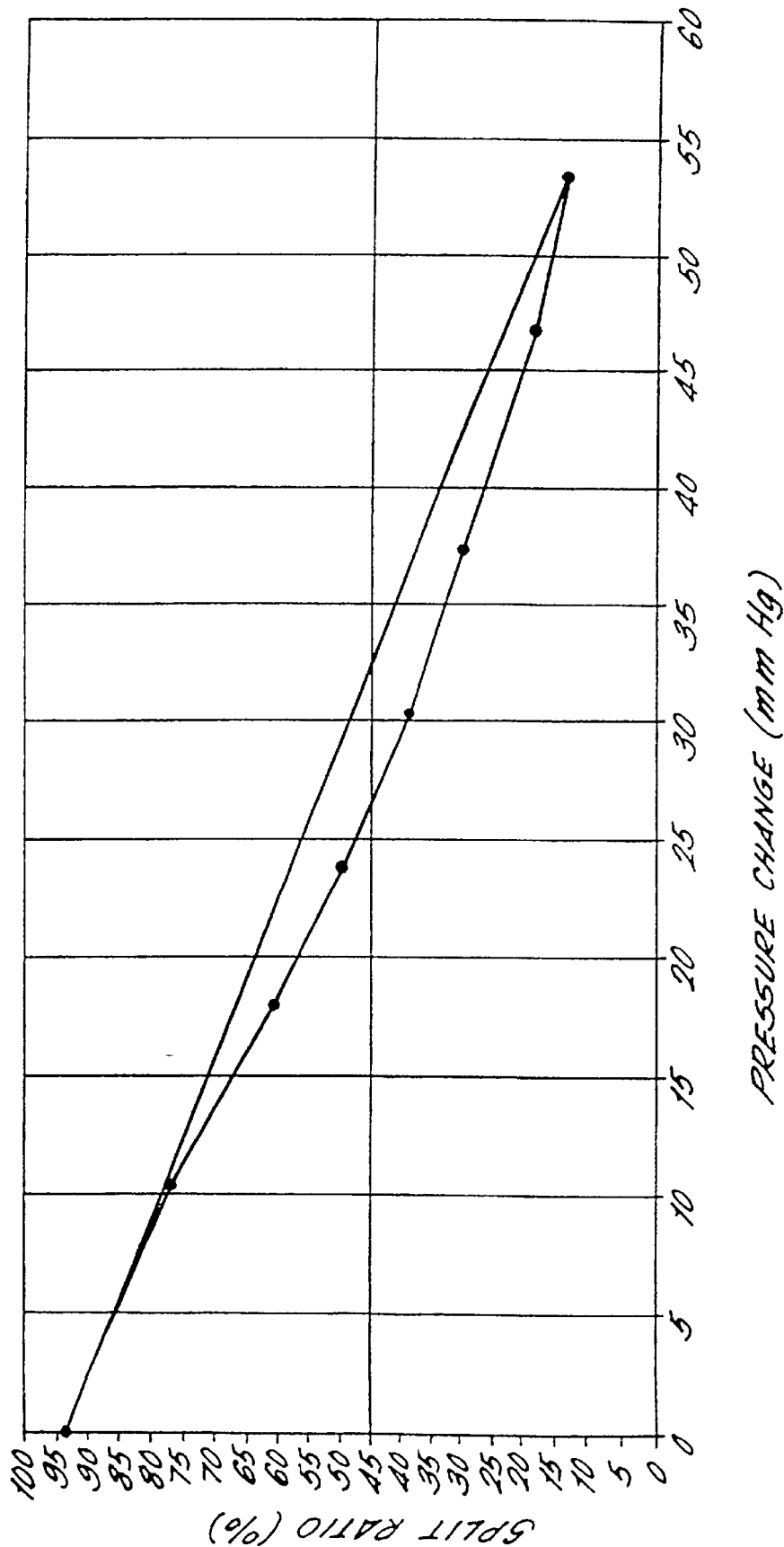
FIG. 14. LOOPED COUPLER PRESSURE GAUGE

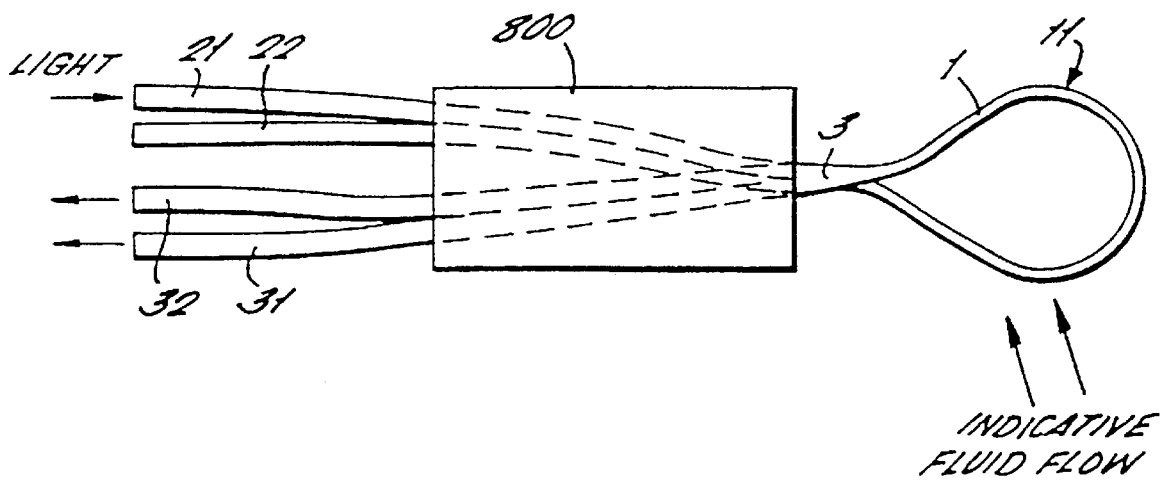
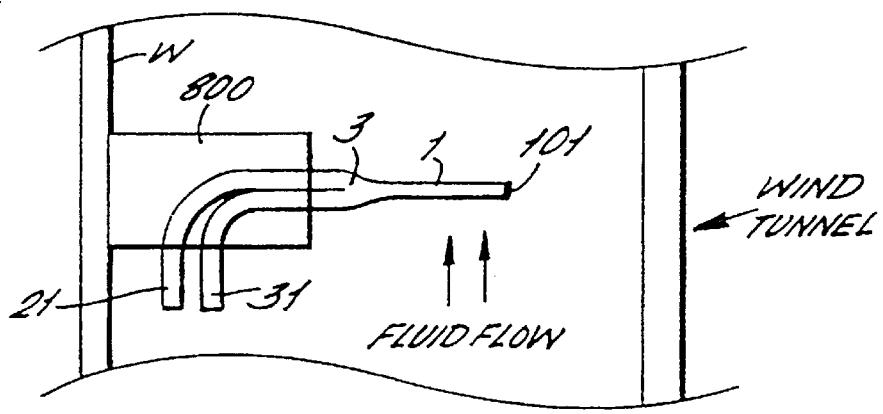
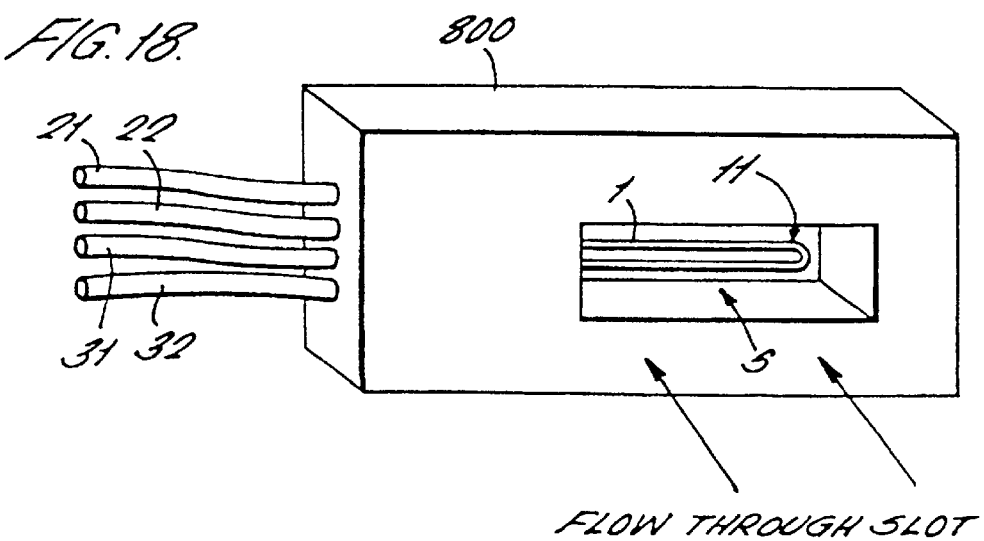

FIBEROPTIC COUPLER SENSOR AND A MEASUREMENT METHOD

This application is a national stage filing under 35 U.S.C. §371 and priority is hereby claimed on International Application No. PCT/GB99/03124, Filed Sep. 20, 1999, which International Application was published in English as No. WO 00/17608.

The present invention relates to sensing apparatus employing optical fibres, and in particular, although not exclusively, to sensing apparatus incorporating optical fibre sensors mounted in catheter probes for medical applications such as in-vivo measurement of pressure.

Sensors for particular measurands, such as pressure, temperature, and strain, are often required to be as small as possible, and this is particularly true for in-vivo medical applications. Sensors are also often required to be passive, ie. requiring no electrical power input in order to function, or to dissipate negligible or zero power during operation.

Optical sensors are good candidates for applications having these requirements, and indeed optical sensors that exploit optical fibre technology are most attractive devices for application in medical procedures associated with diagnosis and intervention. They have a number of important advantages over more classical sensors (eg. electronic), namely, their small size, immunity to EM-noise, high degree of bio-compatibility, high sensitivity, ease of sterilisation, and passive operation. However they often necessitate the use of complex and expensive optics and electronics as is the case with interferometric based optical fibre sensors. It is therefore desirable to reduce the complexity and cost of fibre optic sensing apparatus.

Fibre optic sensors based on numerous principles of operation are well-known, including those based on interferometry, non-linear effects, fluorescence (e.g. as a function of temperature), dimensional changes of in-fibre Bragg gratings, and amplitude modulation of light signals. Both extrinsic and intrinsic amplitude modulation sensors are known. In extrinsic amplitude sensors, light exits from an optical fibre and the sensor is configured such that a varying amount of light is recaptured in another or the same fibre, the amount being dependent on the particular measurand. Some of the light input to the device is therefore lost, reducing the power of the recaptured signal. Furthermore, the power of the recaptured signal, rather than being a function of the measurand only, is instead dependent on the input light power, which may vary.

Intrinsic amplitude sensors have typically involved the measurand interacting with an optical fibre and leading to a variation in light loss in the fibre. Such interaction usually takes the form of squeezing or flexing the fibre such that micro bending loss occurs, and again input light power is lost and the output is affected by fluctuations in the input light power.

Any fibre optic sensors which rely on the intensity of the output signal have the inherent disadvantage of being sensitive to variations in the power level of the light source.

It is desirable, therefore, to provide sensing apparatus and a measurement method which address the problems associated with the prior art.

According to a first aspect of the present invention there is provided Sensing apparatus including:
a sensor comprising
a fused tapered fibre optic coupler formed of two optical fibres fused together to provide a fused portion which is drawn down to form a taper waist portion, the coupler having an input end comprising an input unfused portion of one of said two optical fibres and an output end comprising an output unfused portion of one of said two optical fibres;
a light source arranged to input light to the taper waist portion along the input unfused portion; and a light detector arranged to generate a signal indicative of a parameter of the light transmitted to the output unfused portion from the taper waist portion,
characterised in that the taper waist portion is formed as a loop and at least part of the loop is arranged to bend in response to a measurand.

The sensor may further comprise bending means arranged to bend at least part of said loop according to the measurand.

The parameter of the light, of which the generated signal is indicative, may for example be the light power, intensity, or wavelength.

The fused tapered coupler may be a typical 2×2 device comprising two unfused input portions and two unfused output portions, or may be formed from three or more optical fibres.

Alternatively, the fused tapered coupler may have only one unfused input portion. Such an arrangement may be formed by cutting off or otherwise removing one of the input portions of a 2×2 coupler, or by suitable coupler fabrication.

Similarly, the output end may comprise a single infused output portion, or two or more unfused output portions.

The light source may be a simple light source, such as a LED. The taper waist portion typically has a substantially uniform cross sectional area along its length, and the drawing down process, which, in the art, is also referred to as "tapering" or "elongation" or "pulling", results in that cross sectional area being smaller than the sum of the cross sectional areas of the unfused fibres. Fusing together and drawing down (i.e. pulling in a controlled fashion) the optical fibres enables optical interaction between them. Thus, although in certain embodiments light is input to the sensor along only one unfused "input" fibre, in general not all of the light reaching the output end will be transmitted to one output unfused portion. In embodiments where the output end comprises two unfused output portions, in general the total light power emerging from the device along the output fibres will be shared between them. A splitting ratio may be defined as the ratio of the light powers propagating in the two unfused output fibres, but is often defined in terms of the light power in one output fibre expressed as a fraction or is percentage of the total emerging power.

The optical field within the tapered portion is very sensitive to changes in geometry, and bending the loop will, in general, result in a change in the splitting ratio. The term "bending" is used to denote any action resulting in deformation, deflection, distortion or change in the curvature of the loop, in part or as a whole.

In embodiments where the output end comprises a single unfused portion, deformation of the loop, in general, results in a change in a parameter of the light transmitted to the output portion, for example a change in its intensity.

The sensor is arranged so that the bend applied to the loop is in accordance with the quantity being measured by the sensing apparatus, i.e. the measurand. Thus the applied bend is a substantially reproducible function of the measurand. For example, the end of the loop may be deflected sideways by a distance proportional to the magnitude of the measurand.

Changes in the measurand result in changes in the bend applied to the loop, and hence changes in the splitting ratio. This in turn leads to a change in the signal generated by the light detector, which can therefore be used to monitor the measurand.

This first aspect of the present invention provides numerous advantages including:

a) By arranging the taper waist portion as a loop, the sensor can have a probe-like form, with input and output fibres at the same "end" of the loop;

b) An indication of the measurand can be obtained by simply monitoring the magnitude or other aspect of the signal from the light detector, using for example a photodiode. The sensing apparatus may thus have low complexity and cost;

c) As the parameter of the light transmitted to the output unfused portion (or the splitting ratio) is very sensitive to changes in the geometry of the taper waist region, the bending means may be engineered in a wide variety of ways, to suit particular applications. Providing that the bend applied to the loop is in accordance with the measurand, i.e. a substantially reproducible function of the measurand, then the generated signal will be a useful indication of the measurand. Thus, there is considerable design freedom. In addition, reproducable bending may be easier to engineer than the application of positive axial strain. Also, the loop need not be encapsulated in a holding medium. This produces the advantage that light propagating in the taper waist portion may be strongly confined, reducing losses;

d) The sensing apparatus comprises a passive sensor. In effect, the sensor is an intrinsic amplitude modulated device, but advantageously does not modulate amplitude by varying loss. Instead, the light transmitted to the output fibre (or the splitting ratio) is modulated, and the sensor can thus deliver a stronger output signal.

Advantageously, the loop may have been annealed after its formation. In the annealing process the loop is heated (typically by a flame) sufficiently for stresses caused by the bending of the taper waist portion to form the loop to be relaxed, but without causing significant additional loss of output power. Annealing can improve the stability of the loop and/or its mechanical reliability.

The loop may be nominally planar (i.e. it is formed in a plane and/or it lies substantially in a plane when no force is applied to it by the bending means) and the bending means may be arranged to bend the loop substantially in or out of this nominal plane.

Advantageously, the output end may comprise two unfused output portions of optical fibre and the sensing apparatus may comprise a second light detector, the two light detectors being arranged to generate respective signals indicative of parameters of the input light transferred to each of the output unfused portions (i.e. the nominal output fibres). The signals may then be combined in such a way so as to provide an output signal that is indicative of the measurand and is independent of the input power. For example, the output signal may vary in proportion to the ratio of the respective signals or the ratio of the difference between the signals to their sum.

According to an embodiment of the present invention there is provided sensing apparatus including:

a sensor comprising
  a taper waist portion of optical fibre formed by fusing together and drawing down respective portions of two optical fibres,
  a first taper transition portion of optical fibre at a first end of the taper waist portion, optically connecting the taper waist portion to a first two respective unfused portions of said two optical fibres and being a portion over which a transition from the taper waist portion to said first two respective unfused portions occurs, and
  a second taper transition portion of optical fibre at a second end of the taper waist portion, optically connecting the taper waist portion to a second two respective unfused portions of said two optical fibres and being a portion over which a transition from the taper waist portion to said second two respective unfused portions occurs, the apparatus further including
a light source arranged to input light to the taper waist portion along one of said first two respective unfused portions; and
a light detector arranged to generate a signal indicative of a parameter of the light transmitted to one of said second two respective unfused portions from the taper waist portion,
characterised in that the taper waist portion is arranged as a loop and the sensor further comprises bending means arranged to bend at least part of said loop according to a measurand.

Conveniently, the optical fibre portions of embodiments of the present invention may be provided by a pre-formed fused tapered 2×2 bi-directional coupler. These devices are well-known and are formed by holding in contact and stretching and fusing along a section two optical fibres in a heat source such that optical interaction between the fibres becomes possible. Typically, these devices are fixed and packaged such that the fibres are held taut. A 2×2 device has two input and two output fibres, and "bi directional" indicates that the roles of the nominal inputs and outputs can be interchanged. Clearly, fused tapered couplers having other numbers of input and/or output fibres may be used in embodiments of the present invention. A schematic diagram of a known fused tapered coupler is shown in FIG. 1. The taper waist portion 1 has a reduced cross sectional area. The taper waist is also known as the taper neck. Taper transition portions 2,3 optically connect the taper waist 1 to unfused portions 21,22 and 31,32 of the input and output fibres respectively. These devices are also known as fused bi-conical tapered couplers as the taper transition portions are substantially conical. It is known to control the fusing and drawing down (tapering) process to give a desired taper transition portion profile. A linear taper is known to be stiffer, i.e. mechanically more resistant to bending, than exponential transitions.

Advantageously, the optical fibres may be single mode (also known as mono mode) fibres. Such fibres comprise a core surrounded by a sheath of cladding material having a lower refractive index (n) than the core. The core is typically circular with a sufficiently small diameter such that only the fundamental mode can propagate down the untapered fibre. This fundamental mode is guided in the untapered fibre by the core-cladding boundary. The core diameter is typically smaller than 15 $\mu$m but other sizes are also known. By employing single mode fibres and inputting light down only one of the unfused input fibres, more pronounced variations in splitting ratio with bending can be achieved than with multimode fibres. The taper waist portion may be drawn down to such an extent that the core material—cladding material interface in the waist is no longer practically able to confine and guide the fundamental mode. In this situation, the fundamental mode is strongly guided by the cladding material external boundary (typically the interface with air) as it propagates down the taper waist, and the cores no longer play a role. Initially, the fundamental mode propagates along the input fibre (unfused) guided by the fibre core. On entering the first taper transition section it sees a core of gradually reducing radius. There comes a point where the core is too small to guide the fundamental mode, which then "breaks out", to be guided by the cladding—air interface, i.e. the propagating field is now over the entire waist cross section.

It is known that a sufficiently tapered region of a single mono mode fibre is less prone to bend loss than the untapered fibre because the fundamental mode, is previously weakly confined by the core, is strongly confined in the tapered region by the cladding—air boundary. For example, in the paper "Miniature High Performance Loop Reflector", Oakley et al, Electronics Letters Dec. 5th, 1991 Vol. 27 No 25 pp 2334–2335, it is reported that a 1.5 mm diameter bend can be formed without introducing measurable loss (i.e. in this case less 0.05 dB) in a tapered waist region of a single mode fibre, the untapered fibre having a core diameter of 10 $\mu$m, a cladding diameter of 125 $\mu$m, and a cut-off wave length of 1250 nm, and the cladding diameter in the taper waist originally reported as being 30 $\mu$m. The true cladding diameter in the taper waist was in fact 15 $\mu$m, as was reported in a correction published later. In contrast, the minimum bend diameter of the untapered fibre consistent with low loss was approximately 4 cm.

It has been determined that in embodiments of the present invention, by drawing down the optical fibres sufficiently to ensure detachment of the input fundamental mode field from the input fibre core in the taper transition region, the loop in the taper waist portion can incorporate a sharp bend with negligible additional loss. Advantageously, the taper waist portion may have a diameter of less than 50 $\mu$m.

Preferably, the taper waist portion may have a "diameter" of 30 cm or smaller. In general, the smaller the diameter of the taper waist the tighter the bend which can be made to form the loop without introducing unacceptable loss. However, the minimum diameter is determined by the wavelength of the light that the waist is intended to guide.

The loop may incorporate a bend having a diameter of 2 mm or less, and may be substantially, U-shaped, incorporating a 180° bend. Advantageously for medical applications, the bend diameter may be 1 mm or smaller.

The size of the loop may therefore be reduced, to produce a compact sensor. Advantageously, the U-shaped loop enables the sensor to be arranged in a probe-like form. Sensors incorporating U-shaped loops with 180° bends over diameters smaller than 1 mm are particularly suitable for medical applications and may be arranged inside catheters for in-vivo measurements.

Conveniently, the optical fibre portions of preferred embodiments of the present invention may be provided by fused tapered 2×2 bi-directional couplers preformed from single mode fibres. Again, such devices are well-known, and an example is shown in FIG. 2. Each untapered fibre 21,22,31,32 comprises a core 211,221,311,321 surrounded by cladding 212,222,312,322. In the taper waist section 1 the cores have been reduced in cross section by the tapering process by such an extent that they no longer play a role in guiding light. The nominal positions of the respective cores in the taper waist portion are shown as broken lines 111,121.

Numerous models have been proposed for the mechanism by which light power input to only one of the input fibres 21,22 is shared between the two outputs 31,32. One of the most satisfactory explanations is as follows (see for example "Analyse d'un coupleur bidirectionnel a fibres optiques monomodes fusionnees", Bures et al, Applied Optics, Vol 22, No 12, Jun. 15, 1983 pp 1918–1922). The fused tapered waist portion 1 can be regarded as a single guide for the optical field, as the cores are too small in this region to play any part. The cladding of this single guide is the surrounding air. The fundamental mode propagating down one of the input fibres, say fibre 21, initially confined in the core 211, on entering the tapering transition region 2 sees a core which is reducing in size. There comes a point where this fundamental mode can no longer be confined by the core 211 and it "breaks out", to be confined now by the "single guide" comprising the whole cladding material cross section in the taper waist 1. In effect, the single guide that is the taper waist is being excited on only one side as a result of light being input along only one of the input fibres. A schematic cross section of the taper waist 1 along line A in FIG. 2 is shown in FIG. 3($a$). This figures shows the excitation of one side of the single guide schematically, using an arrow to represent the electric field. This excitation of one side can be regarded as a superposition of the two lowest order modes of the single guide—the fundamental mode and an antisymmetric mode, as shown in FIG. 3($b$). These two modes have different propagation constants (i.e. they propagate at different velocities along the single guide) and their superposition along the taper waist results in a beat pattern, the periodicity of which is determined by the difference between these propagations constants.

For a perfectly symmetrical coupler at certain positions along the taper waist the electric fields of the two modes will exactly cancel in one half of the single guide, and combine to give a maximum value in the other. Moving along the waist, the situation will then reverse. Thus, energy passes alternately from one side of the single guide to the other as we move along the waist. The splitting ratio of power in the output fibres 31,32 therefore depends on the position of the second taper transition region 3 with respect to the beat pattern, i.e. it depends on the distance the two modes have to travel along the single guide before the light field is recaptured by the cores 311,321 of the separate outputs. Thus, the splitting ratio is a function of the length of the taper waist portion 1.

Variations in splitting ratio can be achieved by applying positive axial strain to the taper region, and a sensor based on this principle is disclosed in the paper "Ratiometric fibre-optic sensor utilizing a fused biconically tapered coupler", Booysen et al, SPIE Vol. 1584 Fibre Optic and Laser Sensors IX (1991), pp 273–279.

For a perfectly symmetrical coupler (i.e. formed from essentially identical fibres) held straight, the above model explains the observed results well. The maximum splitting ratio (MSR) that can be achieved is 100% i.e. all of the output power may be in one fibre or the other. When the taper waist is bent, however, the model is difficult to apply. Also, when the taper waist is bent in the nominal plane of the fibres, there is now a structural distinction between the part of the single guide on the inside of the bend, and that on the outside. The MSR is no longer constrained by symmetry and can take any value. A MSR less than 100% means that it is not possible to have all of the output power in either of the output fibres. One of the fibres will be unable to carry more than a maximum amount, less than 100%, of the total output power. "Wavelength-flattened response in bent fibre couplers", O'Sullivan et al, Electronics Letters, Jul. 30th, 1992 Vol 28 No. 16 pp 1485–1486, describes the variation in MSR of a symmetric fused tapered coupler in singelmode fibre as a function of bend angle when the taper region is bent in the plane of the fibres. The taper waist region is initially straight and the purpose of the bending is to give the coupler a wavelength-flattened response.

A similar situation applies when the taper waist region has been formed from dissimilar optical fibres, for example, fibres of different diameters. In general, one of the output fibres will be unable to carry all of the output light.

These asymmetric effects may be thought of as resulting from unequal excitation of the two modes described above, i.e. as the two modes are launched down the taper waist, the input power is shared between them unequally.

Rather than being treated as a single guide, the taper waist may instead be considered as two separate guides which are affected differently by bending in their common plane.

In general, the dependence of the splitting ratio on loop or taper waist portion deformation, exploited by embodiments of the present invention, is a result of a combination of factors, which may include: the beating pattern of modes having different propagation constants; the symmetry of the taper waist; the orientation of the loop with respect to the taper waist symmetry; the direction or plane of bending; and a symmetry resulting in the unequal excitation of modes. Calculation of this dependence is likely to be complicated, and in practice the sensors of embodiments of the present invention will simply be calibrated against the particular measurand.

In preferred embodiments of the first aspect of the present invention, the loop may be nominally planar when no force is being applied to it by the bending means. The bending means may be arranged to bend the loop in its plane, or, alternatively, out of its plane. This may be achieved by applying a force to the tip of the loop, furthest from the taper transition portions, with the unfused portion of the sensor (e.g. the inputs and outputs) held fixed. Accurately reproducible deformation may therefore be achieved without the need for high complexity engineering, thereby facilitating design and improving design flexibility.

In embodiments where the taper waist portion has been formed from nominally identical fibres with circular cross sections, and as a result possesses two axes of substantial symmetry, the loop may be formed by bending the taper waist in the plane of the minor axis of symmetry, i.e. in the "easy" direction. Here, "minor" is used to denote the axis of symmetry on which the taper cross section has the shorter projection. In such an embodiment, the bending means may be arranged to bend the loop out of its nominal plane, i.e. bending takes place parallel to the major axis of symmetry. This configuration provides the advantages that:

a) The loop is stiffer, i.e. more resistant to deformation, in this direction, which can enable more accurately reproducible measurements to be achieved;

b) The loop deformation is such that the portions of the taper waist corresponding to the constituent optical fibres are strained asymmetrically. This can result in more pronounced variation of splitting ratio for a given change in the measurand.

According to a second aspect of the present invention there is provided sensing apparatus including:

a sensor comprising
   a taper waist portion of optical fibre formed by fusing together and drawing down respective portions of at least two optical fibres, the taper waist portion having a first end and a second end, and
   a taper transition portion of optical fibre optically connecting the first end of the taper waist portion to at least one unfused portion of optical fibre, each unfused portion being an unfused portion of a respective one of said at least two optical fibres; and
a light source arranged to input light to the first end of the taper waist portion along one of said at least one unfused portions,
characterised in that the sensor further comprises
   means for reflecting at least some of the input light propagating along the taper waist portion from the first to the second end back along the taper waist portion to the first end,
the sensing apparatus further comprises
   a light detector arranged to generate a signal indicative of a parameter of the reflected input light transmitted to one of said at least one unfused portions from the first end of the taper waist portion, and
   at least part of the taper waist portion is arranged to bend in response to a measurand.

Advantageously, the sensor may further comprise bending means arranged to bend at least part of the taper waist portion according to the measurand.

This second aspect provides all of the advantages listed for the first aspect, with, of course, references to "the loop" now being replaced by "the taper waist portion".

As a result of light being input to and output from the same end of the taper waist region, the sensor conveniently may have a probe-like form.

In its simplest form the sensor may comprise just one unfused portion of optical fibre which is used for both input and output. Of course, in the taper waist region, optical coupling between the fused, tapered optical fibres and bending results in changes in a parameter of the light "recaptured" by the unfused portion after reflection.

Having only one input/output fibre provides the advantage that the size and complexity of the sensor are minimised, and the sensor may be incorporated in a probe of small diameter.

Such a sensor may be produced, for example, from a standard fused tapered coupler by removing one of the nominal input fibres.

Reflection of the input light may be achieved in a variety of ways. For example, in certain embodiments the sensor tapers out from the second end, connecting to unfused portions of the optical fibres, the ends of which are terminated at reflecting surfaces, or joined to provide longitudinal optical connection. Such sensors may be formed, for example, from a conventional fused tapered coupler, with the ends of the output fibres cleaved (to provide reflecting surfaces) or joined.

Alternatively, the reflection may be achieved by arranging the taper waist portion to terminate at the second end at a substantially planar surface, produced, for example, by cleaving (cutting). Again, such a sensor may be formed from a conventional 2×2 fused tapered coupler, by cleaving the taper waist portion.

The taper transition portion may connect to two unfused portions of optical fibre (corresponding, for example, to the two nominal input fibres of a conventional coupler).

Light may thus be output from the sensor along a nominal input fibre of the coupler.

By employing a single pair of fibres as both inputs and outputs, and by reflecting light back from an end of the taper waist rather than looping it, the size and complexity of the sensor have been further reduced.

The reflecting end of the taper waist may have been produced by cleaving (cutting) and may be mirrored to increase the portion of input light reflected back along the taper waist. Reflection may, however, be achieved by other means, such as by looping and fusing the end of the taper waist back on itself.

In embodiments where the taper transition portion connects to two unfused portions, as with the first aspect, a second light detector may be provided, so that signals indicative of a parameter of the light transmitted to each unfused portion may be generated. An output signal dependent on the measurand but independent of the input power may be generated by suitable means.

Again, the optical fibre portions of the second aspect of the invention may conveniently be provided from a known fused tapered 2×2 bi-directional coupler which may comprise monomode fibres as before. For use in apparatus according to this second aspect, these known devices may be cleaved at some point along the taper waist only one half of the cleaved structure is then required.

Advantageously, the length of the taper waist portion may be selected to give a desired stiffness.

The mechanisms by which bending of the taper waist portion alters the splitting ratio of light power transmitted back along the unfused portions of fibre are the same as those described above with reference to the first aspect.

Advantageously, the taper waist portion and the two unfused portions may be substantially co-planar, and the bending means may be arranged to deflect the taper waist portion in this plane, the unfused portions being held fixed. This plane will typically be parallel to the major axis of symmetry of the taper waist portion and so deflection in this plane will result in unequal straining of the two "halves" of the taper waist portion, corresponding to the respective. constituent fibres. Again, this unequal straining can lead to more pronounced variation in splitting ratio for a given deflection.

In embodiments of either the first or second aspects, the taper waist portion may have a substantially uniform cross section, with at least a major axis of symmetry in a direction corresponding to a line joining the nominal centres of the constituent fibres during the fabrication process (fusing and drawing down). The cross section may be circular,eliptical, figure of eight resembling two overlapping circles,or any other shape depending on the shapes and sizes of the constituent fibres and the degree of fusing. Of course, the two fibres need not be the same shape or size.

Advantageously, the fibres may be fused together to such an extent that the taper waist portion has a substantially circular cross section. This is advantageous as a circular cross section is a more repeatable cross section than other geometries. Although there is no geometrical major or minor axis of symmetry, there is a functional major axis defined by the orientation of the transition region connecting the unfused portions to the waist.

Advantageously, the measuring apparatus may further comprise a tubular probe body, and the bending means may comprise a resilient membrane arranged to deflect according to a pressure difference between regions inside and outside the probe body. The sensor may be arranged inside the probe body, at one end, with the taper waist portion extending towards the end, and the input/output fibres running back along the probe. In this embodiment, the deflection of the membrane is communicated to the taper waist portion, which may in accordance with the first aspect be a loop, and the splitting ratio is modulated according to the pressure difference.

The membrane may seal an angled end of the tubular probe body, and may be in direct contact with the taper waist portion. The taper waist portion or loop may be arranged to lie nominally along the longitudinal axis of the probe. Advantageously, in this arrangement, deflection of the membrane bends the taper waist portion off the axis, i.e. out of its plane.

The probe body may comprise both flexible and rigid sections and may comprise a rigid section at or nearer to one end. The membrane may seal an orifice in the rigid portion. The probe body may be a catheter and may have an outer diameter of 1 mm or less.

According to a third aspect of the present invention there is provided a sensor comprising a fused tapered fibre optic coupler formed of two optical fibres fused together to provide a fused portion which is drawn down to form a taper waist portion, the coupler having an input end comprising an input unfused portion of one of said two optical fibres and an output end comprising an output unfused portion of one of said two optical fibres, characterised in that the taper waist portion is formed as a loop.

The sensor may further comprise bending means arranged to bend at least part of the loop according to the measurand.

The body may comprise a substantially rigid section and the input and/or output portions may be attached to the rigid portion. The attachment may be substantially rigid, using for example epoxy resin or clamping means, or less rigid, using for example silicone rubber. The attachment means restricts the movement of the input and/or output unfused portions with respect to the rigid portion.

The bending means may be arranged to deflect the loop with respect to the rigid portion.

According to a fourth aspect of the present invention there is provided a sensor comprising a taper waist portion of optical fibre formed by fusing together and drawing down respective portions of at least two optical fibres, the taper waist portion having a first end and a second end, and a taper transition portion of optical fibre optically connecting the first end of the taper waist portion to at least one unfused portion of optical fibre, each unfused portion being an unfused portion of a respective one of said at least two optical fibres, characterised in that the sensor further comprises means for reflecting light propagating along the taper waist portion from the first to the second end back along the taper waist portion to the first end.

The sensor may further comprise bending means arranged to bend at least part of the taper waist portion according to a measurand.

Again, the body may comprise a substantially rigid portion and one or more of the unfused portions may be attached to the rigid portion.

According to a fifth aspect of the present invention there is provided a measurement method comprising the steps of:

forming a loop from a fused taper waist portion of a fused tapered fibre optic coupler;

inputting light to the taper waist portion along a nominal input fibre of the coupler;

distorting said loop according a measurand;

generating a signal indicative of a parameter of the light transmitted to a nominal output fibre of the coupler from the taper waist portion; and using said signal to provide an indication of the measurand.

Advantageously, the method may also include the step of annealing the loop.

According to a sixth aspect of the present invention there is provided a measurement method comprising the steps of:

inputting light to a taper waist portion of a fused tapered fibre optic coupler along a nominal input fibre of the coupler;

reflecting at least a portion of the light propagating along the taper waist portion from the input fibre back towards the input fibre;

generating a signal indicative of a parameter of the reflected light transmitted to a nominal input fibre of the coupler from the taper waist portion;

distorting at least part of the taper waist portion according to a measurand; and using the signal to provide an indication of the measurand.

According to a seventh aspect of the present invention there is provided a measurement method comprising the steps of:

inputting light to a portion of optical fibre being optically connected at one end to at least two nominal output optical fibres, the inputted light being distributed non-uniformly over a cross section of said portion;

bending said portion according to a measurand;

generating a signal indicative of a ratio of respective light powers transferred to each of said nominal output optical fibres from said portion, and using said signal to monitor said measurand.

A non-uniform distribution of input light may be achieved by exciting only part of the cross section with optical field, for example by inputting light down only one of two input fibres fused and connected to the portion. However, the intensity of input light may be varied across the cross section in some other way, and may be non zero across the entire cross section.

In certain embodiments, light of different wave lengths may be input to different parts of the cross section. In general, any non-uniform distribution of input light over the cross section may be used which results in the splitting ratio being dependent on the geometry of the optical fibre.

Embodiments of the present invention will now be described with reference to the accompanying drawings in which:

FIG. 1 is a schematic diagram of a known fused tapered coupler suitable for use in embodiments of the present invention;

FIG. 2 is a schematic diagram of a known fused tapered monomode coupler suitable for use in embodiments of the present invention;

FIG. 3 is a highly schematic diagram of the electric field patterns of modes at the input end of a tapered waist portion excited by light from only of its input fibres;

FIG. 8 is a schematic diagram of different parts of a sensor embodying the present invention;

FIG. 9 is a schematic diagram of sensing apparatus in accordance with a further embodiment of the present invention;

FIG. 10 is a schematic diagram of different views of part of a sensor in accordance with an embodiment of the present invention;

FIG. 11 is a schematic diagram of the end of a probe for measuring pressure in accordance with an embodiment of the present invention;

FIG. 12 is a schematic diagram of part of a sensor embodying the present invention;

FIG. 13 is a schematic diagram of a probe for measuring pressure in accordance with an embodiment of the present invention;

FIG. 14 is a graph showing the variation of splitting ratio with pressure for the probe of FIG. 13;

FIG. 15 is a schematic diagram of the probe in accordance with a further embodiment;

FIG. 16 is a schematic plan view of a sensor embodying the present invention;

FIG. 17 is a schematic diagram of a sensor embodying the present invention and mounted in a wind tunnel to monitor fluid flow;

FIG. 18 is a schematic diagram of a further embodiment, suitable for sensitive measurement of fluid flow;

Figure 4:
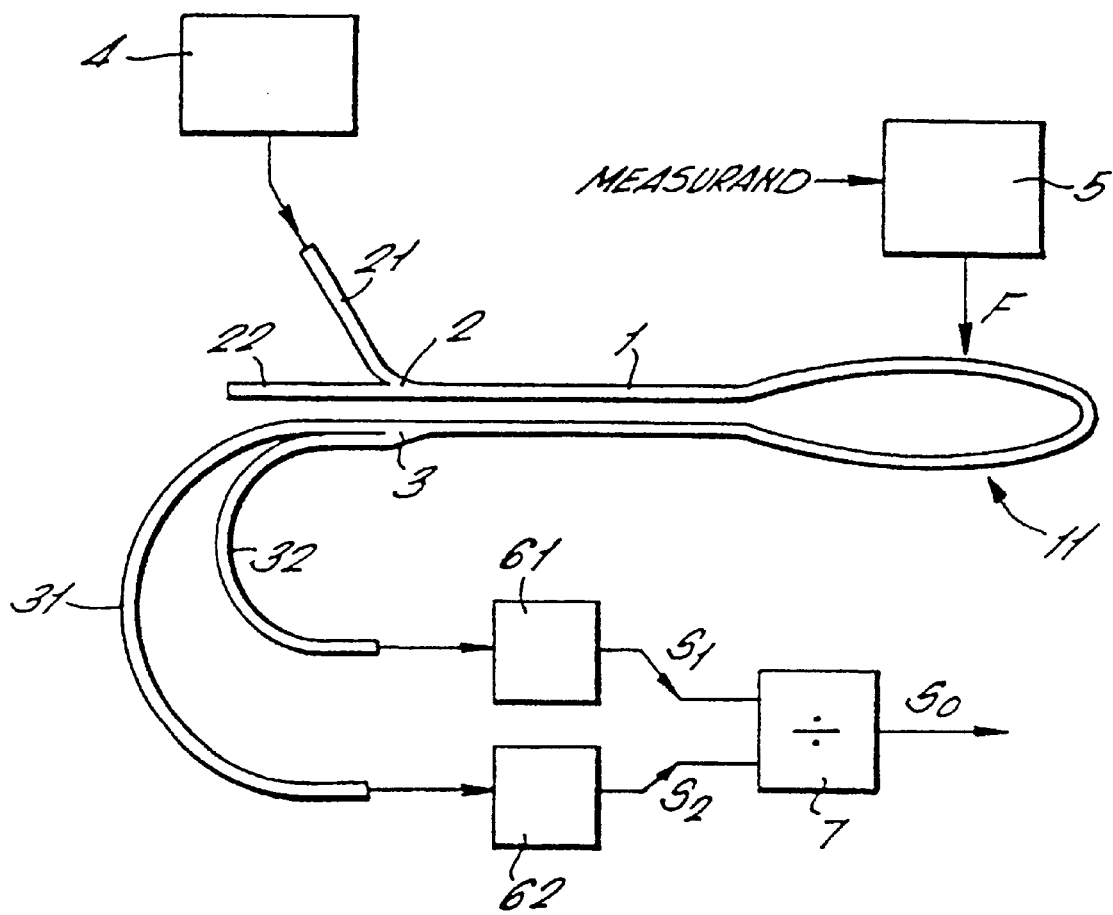
FIG. 4 is a schematic diagram of sensing apparatus in accordance with an embodiment of the present invention.

Referring now to FIG. 4, sensing apparatus in accordance with an embodiment of the invention comprises a light source 4 arrange to input light to an unfused portion 21 of optical fibre. This portion of fibre 21 is fused to a second portion 22 and tapered down over a taper transition region 2 to form a taper waist section 1. The taper waist 1 is looped back on itself, forming a loop 11, before splitting into separate output optical fibres 31,32 over a second taper transition portion 3. Bending apparatus 5 responsive to changes in a measurand is arranged to bend the loop 11 by applying a force F. The measurand in this example is magnetic field and the bending apparatus 5 contains a component with a dimension which varies in proportion to the magnitude of the applied magnetic field. In other examples the measurand may, for example, be pressure, temperature, electric field, length, or strain. Light propagating around the loop 11 in the taper waist 1 is split at the second taper transition portion between the two output fibres 32,31. In general, the split will not be equal and the light signals emerging from the two output fibres will have different intensities. Light detectors 61,62 generate respective signals S1,S2 proportional to the signal powers from the two outputs 31,32 and a divider 7 produces an output signal $S_o$ proportional to the ratio of S1 to S2. The output signal $S_o$ is, therefore, independent of the output power of the light source 4.

Changes in the measurand cause the force F applied to the loop 11 by the bending apparatus 5 to vary, and results in a distortion of the loop 11, at least part of which is unsupported. The optical field in the taper waist portion is sensitive to the loops geometry, and this distortion results in a change in the splitting ratio at the second taper transition portion 3. thus, the output signal $S_o$ varies according to changes in the measurand. Clearly, if an accurate and reproducable measurement is required, then the bending apparatus 5 should be arranged so that the distortion applied to the loop 11 is itself a reproducible (and ideally a single valued) function of the measurand.

In this example the taper waist cross section has a diameter of 20 microns to enable the loop to be sharply bent.

The unfused portions of fibre 21, 22, 31, 32 can, of course, be any length. The lengths may be chosen to enable the probe or sensor to be remote rom the opto-electronics. In this example, the second unfused input portion 22 is not used, and may be removed, so that the first taper transition portion 2 connects the taper waist portion to just a single unfused input portion 21. Thus, the input end of the coupler may consist of just on input fibre.

Figure 5:
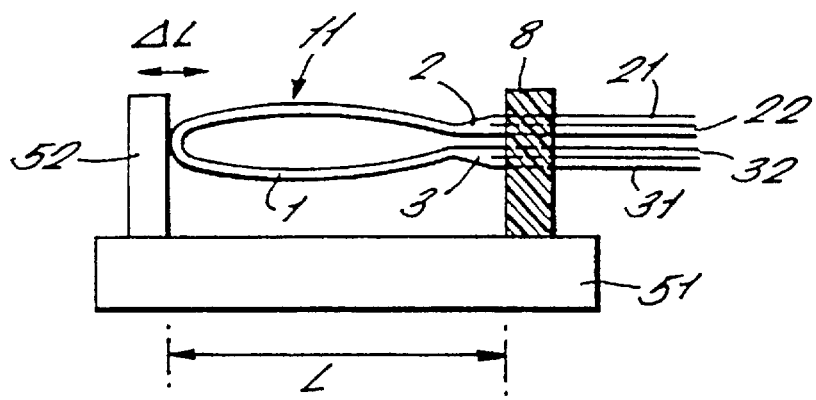
FIG. 5 is a schematic diagram of a temperature sensor embodying the present invention.

Referring now to FIG. 5, a sensor embodying the present invention is arranged so that the loop 11 in the taper waist 1 is deflected according to changes in temperature. In this embodiment, the input and output fibres 21,22,31,32 are fixed in position with respect to an aluminium block 51. This fixing is achieved by encapsulating parts of the unfused fibres in a block of encapsulating material 8, which in this case is epoxy resin. In this example, the resin encapsulates only sections of the unfused input and output fibres and does not extend to the taper transitions 2,3 or the taper waist 1 which remains unsupported and surrounded by air. This ensures that light in the transition and waist portions is strongly confined and so reduces losses.

A protrusion 52 at one end of the block 51 is in contact with the tip of the loop 11 and communicates any changes in the length of the block to the loop 11, causing its curvature to vary also. Aluminium has a high co-efficient of thermal expansion and so the loop 11 is bent according to changes in temperature.

In addition to changing the strain in the loop 11, length changes $\Delta L$ can also change the stress pattern in the taper transition portions 2,3 which are unsupported by the epoxy resin. The splitting ratio is particularly sensitive to changes in the stress and strain patterns at the transition regions and so by encapsulating the fibre optic portions of the sensor in this way the sensitivity of the output to temperature changes can be increased.

However, disturbing the taper transition portions can increase loss, and so to keep losses to a minimum it is preferable to arrange the sensor so that the transition portions are disturbed as little as possible as a result of distorting the taper waist portion.

Figure 6:
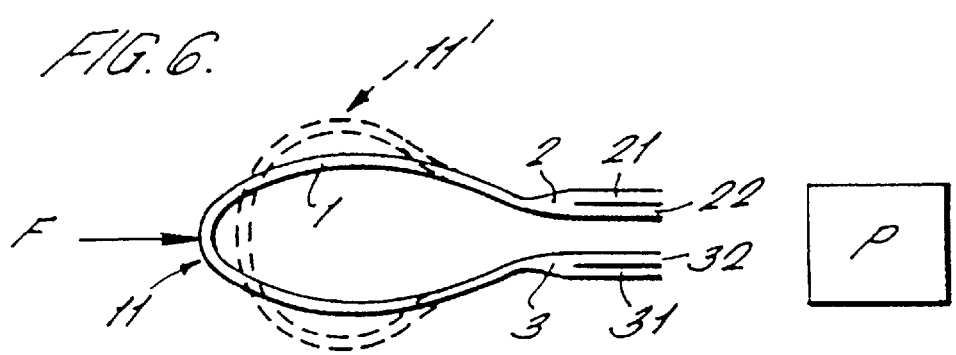
FIG. 6 is a schematic diagram of part of a sensor embodying the present invention.

FIG. 6 shows a plan view of part of a sensor in accordance with a further embodiment of the present invention. In this embodiment, the loop 11 is nominally planar, the plane P of the loop being the plane of the paper. The bending means is arranged to apply a force F to the tip of the loop 11 to cause it to deform in the plane P. The shape of the loop after distortion 11' is shown with broken lines. The magnitude of the force F is dependent on the magnitude of the measured quantity. In this example, the unfused portions of the nominal input and output fibres 21,22,31,32 immediately adjacent to the taper transition portions also lie substantially in the plane P.

Figure 7:
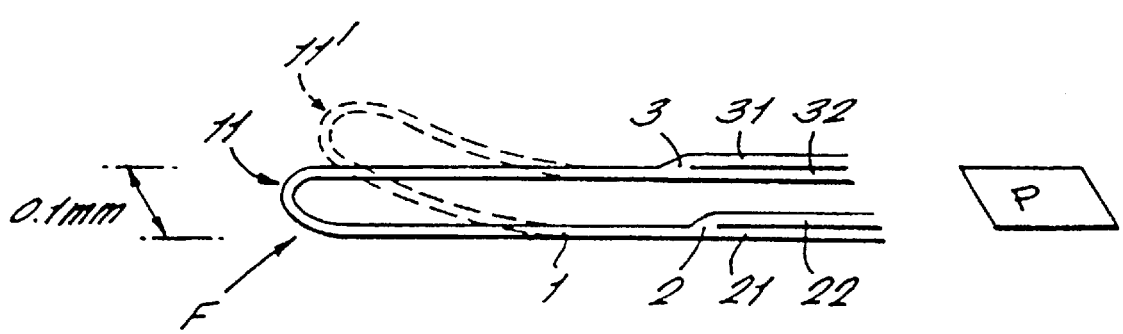
FIG. 7 is a schematic diagram of part of a sensor embodying the present invention.

FIG. 7 shows part of a sensor in accordance with another embodiment. The loop 11 is substantially U-shaped incorporating a 180° bend of diameter less than 1 mm. Conveniently, this gives the sensor a slim, probe-like form. Again, the loop is nominally planer when no force is being applied to it by the bending means, the plane P of the loop lying at an angle to the plane of the paper. The bending means in this example is arranged to apply a force P near the tip of the loop 11, the force F having a component perpendicular to the plane P. The resultant deflection of the loop is, therefore, out of the plane P. an advantage of this configuration is that the distortion of the taper waist 1 is a well defined, predictable, and reproducable function of the applied force F.

Referring now to FIG. 8, in a further embodiment the taper waist portion has a substantially uniform "figure of eight" shaped cross section. This is shown in FIG. 8(*a*) the cross section resembles the shape formed by two overlapping circles of equal diameters. The taper waist 1 has been formed by fusing together two similar monomode fibres, and the residual cores from those fibres lie on a major axis of symmetry A1. As a result of the similarity between the constituent fibres, the taper waist 1 has a further minor axis of substantial symmetry A2.

FIG. 8(*b*) shows a perspective view of the looped taper waist 11, the taper transitions 2,3 and the unfused portions of the input and output fibres 21,22,31,32. Again, the undistorted loop 11 is substantially planar and has been formed by bending the taper waist 1 in a direction perpendicular to the major axis of symmetry A1. Thus, at all positions along the undistorted taper waist, the major axis of symmetry A1 is perpendicular to the plane P. The unfused portions of the input fibres 21,22 are arranged so that their cores are parallel and lie in a plane perpendicular to the plane P. The output fibres are arranged similarly. The taper transition portions 2,3 both have substantially linear profiles. This makes the transition portions stiffer and helps to confine the effects of the bending means to the taper waist portion 1 alone.

FIG. 8(*c*) is a side view of the optical fibre portions of FIG. 8(*b*) mounted on a probe body 9. The input and output fibres 21,22,31,32 are fixed to the probe body 9 with a block of epoxy resin 8 which extends to encapsulate parts of the taper transition portions 2,3. This helps to further increase the rigidity of the taper transitions. The loop 11 of taper waist 1 is unsupported by any encapsulating material and so is free to be distorted. In this example, the bending means 5 takes the form of a block of material fixed at one end to the probe body 9 the opposite end of the block is angled and is arranged to touch the tip of the loop 11. The material is magnetostrictive and so varies in length according to the magnitude of the applied magnetic field. Changes in the length of the block $\Delta L$ are communicated directly to the loop and cause it to bend out of the plane P, taking up a new geometry 11'. The distortion of the loop 11 is, therefore, substantially in a direction parallel to the major axis of symmetry A1 and results in the two halves of the taper waist 1A,1B nominally corresponding to the respective constituent fibres 21,22 being strained unequally. For the particular distortion shown in the figure one half 1A of the taper waist is under compressive strain whilst the other half 1B is under tensile strain. The splitting ratio is particularly sensitive to such asymmetric distortion of the taper waist. In general, this is a result of a combination of two factors, namely that asymmetric strain alters the beat pattern of the two lowest order modes propagating along the taper waist, and secondly, asymmetric distortion of a loop having the geometry shown in FIG. 8 can result in asymmetric stress and/or strain of the taper transition portions which, in this example, are only partially encapsulated. In certain other preferred embodiments the taper transition portions are not encapsulated; only the unfused portions are attached to the probe body 9. Asymmetric stress and/or strain of the input taper transition portion 2 can affect the relative powers of the two lowest order modes launched down the taper waist.

The arrangements shown in FIG. 8(*c*) leads to reproducable bending of the loop 11 as a function of the measurand. The loop 11 has been formed by bending the taper waist portion 1 in the "easy direction" i.e. in a direction perpendicular to the major axis of symmetry. The stiffness of the loop 11 with respect to bending perpendicular to the plane P has been increased by forming the taper transition portions 2,3 with linear profiles and by partially encapsulating them in the block of epoxy resin 8.

Referring now to FIG. 9, in a further embodiment of the present invention, the sensor comprises two unfused portions of optical fibre 31,32 fused and tapered together over a taper transition region 3 to form a taper waist 1 terminated by a reflecting surface 101. The end of the taper waist is shown in more detail in FIG. 9(*b*). The reflecting surface 101 has been formed by cleaving (i.e. cutting) the taper waist and is substantially planar. The reflecting surface is at an angle θ to the nominal longitudinal axis of the taper waist region. In this example θ is acute but ideally should be 900. The reflecting surface 101 has also been mirrored to increase its reflectivity.

Light is input to only one of the unfused portions 31 from an LED via a side branch 33 of optical fibre appropriately spliced to the unfused portion 31. Input light passes through the transition region 3 and propagates along the taper waist 1 to the end surface 101 where it is reflected back along the taper waist. On returning to the transition portion 3 the input light splits between the two unfused portions 31,32. The splitting ratio is a sensitive function of the geometry of the taper waist portion 1. Light travelling back along each of the unfused portions 31,32 from the taper waist 1 is directed to respective photodiodes 61,62 which generate signals S1,S2 indicative of the power splitting ratio. These signals S1,S2 are combined in an adder 63 and a signal indicative of the difference between them is generated by a subtractor 64. The sum and difference signals are then ratioed in a divider 7 to produce an output signal $S_o$ indicative of the splitting ratio and independent of the power output of the LED 4.

In certain other preferred embodiments, the subtractor is not required. In these embodiments one or other of the signals are divided by the sum of the two to obtain a value of the splitting ratio which can vary between 0 and 1. This figure may be multiplied by 100 to give a splitting ratio as a percentage.

In the embodiment of FIG. 9, the bending means is a bi-metallic strip 53 with a protrusion 54 at one end. The curvature of the bi-metallic strip 53 is a function of temperature and changes in this curvature are communicated to the taper waist portion 1 by the protrusion 54. Part of the taper transition portion 3 is encapsulated in a block 8 of silicone rubber and fixed to one end of the bi-metallic strip 53. Part of the transition region 3 remains unencapsulated and so may be distorted as the taper waist portion 1 is bent. The taper transition 3 has been formed with a curved profile 300 to reduce its stiffness. As a result of these features, the splitting ratio is a particularly sensitive function of the bend applied to the unsupported taper waist and part of the transition portion.

Referring now to FIG. 10, in a further embodiment of the present invention the fibre optic portions of the sensor comprise two unfused portions 31,32 of single mode optical fibre fused and tapered down together over a transition region 3 to form a taper waist portion 1 having a substantially uniform eliptical cross section along its length. The end 101 of the taper waist 1 is cut perpendicular to the nominal longitudinal axis of the taper waist to provide a reflecting surface. The eliptical cross section has a major axis of symmetry A1 and the taper waste 1 is arranged so that at all positions along its length A1 lies substantially in a common plane P. The centres of the unfused portions 31,32 are also arranged to lie substantially in the plane P. The bending means is arranged to bend the taper waist portion 1 in the plane P by applying a force F having a component parallel to the plane P with a magnitude dependent on a quantity to be measured.

FIG. 10(a) shows a perspective view of part of the sensor, and FIG. 10(b) shows a plan view. The cores 311,321 of the constituent monomode fibres are reduced in size over the taper transition region 3 and have negligible cross sections in the taper waist portion 1. By negligible, it is meant that the cores in the taper waist are no longer substantially able to confine the fundamental mode propagating into the sensor along one of the fibres 31,32.

The taper waist portion 1 nominally has two halves 1A,1B corresponding to material from the respective constituent fibres 31,32. FIG. 10(b) shows the position of the taper waist 1 after it has been bent in the plane P by the force F, resulting in unequal straining of the two nominal halves, 1A,1B. This asymmetric straining results in a change in the splitting ratio as reflected light from the end 101 is recaptured by the cores 311,321.

FIG. 11 is a schematic cross section of a pressure probe embodying the present invention. A loop 11 of fused, tapered optical fibre 1 is arranged inside a tubular probe body 91 with the tip of the loop in contact with a flexible membrane 55 which seals the end of the probe body 91. Input and output fibres 21,22,31,32 optically connected to the loop at taper transition portions extend along and inside the probe body 91 away from the membrane 55. At a remote point they emerge from the probe body 91 for connection to a light source and signal generators. The loop 11 is supported at a position close to the taper transitions by a supporting device 92 which in this example is in the form of a wedge. In this example, the optical fibre portions of the sensor comprise a fibre optic directional coupler (i.e. two optical fibres laterally fused and pulled giving a splitting ratio of about 50%) which has been stretched in a controlled manner under applied heat so as to taper the waist region 1. The tapered waist region 1 is then looped back on itself and the loop diameter is made as narrow as possible (to enable the probe diameter to be minimised) without introducing unacceptable loss. Thus, both the input and output fibres 21,22,31,32 enter and exit from the same side.

In general, the splitting ratio (SR) will change from its initial value during the looping process, but this does not necessarily cause a problem in practice. The coupler can be fabricated initially with a suitably different SR to yield the desired SR after bending, or the coupler can simply be used, whatever the post-looping SR turns out to be. Also, a 50% SR is not essential.

Since the optical field within the tapered region 1 is very sensitive to changes in geometry of the region, the splitting ratio of the coupler can be modulated by simply deflecting the looped region 11. This is achieved by adding the flexible membrane 55 to the end of the tube housing 91. The membrane 55 bends the loop 11 as it deflects due to pressure fluctuations.

Light from a simple light source (e.g. an LED) is fed into one of input arms 21,22 of the coupler and the output from the two output arms 31,32 is monitored by photodiodes. The ratio of the signals corresponds to the splitting ratio that in turn is related to the pressure on the membrane.

Referring now to FIG. 12, in a further embodiment of the present invention parts of the unfused portions of the input and output optical fibres 21,22,31,32 are fixed to a supporting block 92b by an encapsulating block of epoxy resin 8. The epoxy resin block 8 does not extend to encapsulate any of the taper transition portions 2,3 in order to ensure that light is strongly guided in this region by the optical fibre— air interface, so reducing losses. The support block 92b is itself mounted on a rigid part of the sensor body 9. A second block of epoxy resin 81 encapsulates part of the taper waist region 1 and fixes it to a second support block 92a, which again is fixed to the body 9. Thus, only a tip portion of the loop 11 is unsupported. The bending means is arranged to deflect the tip portion by applying a force F. The stiffness of the unsupported tip portion can be controlled by appropriate positioning of the second support 92a and thus the sensitivity of the device may be set.

FIG. 13 shows a further pressure probe embodying the present invention. The principle of operation of the probe is based on the change in optical behaviour, due to deformation, of a looped fused tapered 2×2 bi-directional coupler. A 2×2 fused tapered coupler is formed by holding in contact and stretching and fusing along a section two optical fibres in a heat source such that optical interaction between the fibres becomes possible. The splitting ratio (power transfer ratio) is very sensitive to disturbances of the stretched and narrowed region 1. The fused tapered region 1 is bent through 180° to form a loop 11 in order that it may have a probe-like form (with input and output fibres leading to the sensor tip). Whereas a typical optical fibre will suffer serious optical loss for bend radii below 1 cm, the tapered section of the fibres 1 may be bent with a radius of curvature significantly below 1 mm with negligible loss. In the pressure transducer of FIG. 13, the looped coupler is fixed within a sealed tube 91. The input and output fibres 21,22,31,32 of the coupler emerge from one end of the probe body 91 through a sealing plug 93 of suitable material, such as epoxy resin or silicone rubber. The optical fibres, 21,22,31,32 pass down the tubular probe body 91 and are fixed to a wedge shaped support 92 by an encapsulating block 8 of suitable material. In this example the block 8 comprises epoxy resin and encapsulates part of the taper transition regions as well as parts of the unfused constituent fibres 21,22,31,32. The encapsulating block 8 and support wedge 92 form a seal across the probe body 91. The end of the tubular probe 91 is cut at an angle (i.e. the probe body is terminated obliquely) and a silicone rubber cap 50 is positioned over the angled end. The cap 50 is secured to the probe body 91 by a binding 501. In addition, or alternatively, adhesives may be used. The part of the cap 50 which seals the oblique end of the probe body 91 forms a resilient membrane 55. A volume 94 inside the probe body 91 is therefore sealed off from the volume outside the probe by the membrane 55 and the encapsulating block 8. The membrane 55 therefore deflects with changes in external pressure. The loop 11 is arranged so that it held against the membrane 55 and so deflections of the membrane caused by changes in the pressure difference between the volumes outside and inside the probe are directly communicated to the taper waist. Light is input to one of the coupler inputs 21,22 and is branched off to the two output fibres 31,32. Typically, the nominal splitting ratio will initially be set to be close to 50%, by a combination of suitable coupler fabrication and looping steps. In the pressure probe, the splitting ratio will then vary with applied pressure through the deformation caused to the coupling region 1. the splitting ratio is simply monitored by detecting and ratioing the output signals. Thus, the final output signal is normalised for fluctuations in input power or loss in the system.

In the embodiment of FIG. 13, the probe body 91 is formed from a tube of MRI compatible material having a diameter of less than 1 mm and a length of approximately 1 cm. This embodiment is particularly suitable for use in MRI procedures, where the use of fibre optics offers particular advantages (optical measurements are not effected by and do not interfere with the strong magnetic fields present in the machine). The pressure sensor may have other in-vivo applications equally as important (e.g direct measurement of blood pressure in venous and in the heart, and pressure measurement in the brain for critically ill patients and/or patients with head injuries). This may also have significant relevance to industrial applications.

In general, the materials used to construct the probe will be chosen to suit the particular application. For in-vivo measurements, for example, the materials may be chosen for bio-compatibility and ease of sterilisation.

In certain preferred embodiments the probe body is formed of stainless steel.

FIG. 14 shows a graph of results obtained with a sensor similar to that shown in FIG. 13. The sensor had a measurement range of 50 mm Hg, and a resolution of approximately 0.5 mm Hg. The variation in splitting ratio with pressure change is approximately linear, although of course in general individual sensors may be calibrated in order to avoid the need for assumptions about their likely response.

Range and resolution may be readily altered (either more or less) through modification of the membrane or coupler parameters. The absolute resolution possible is limited by the available deformation of the membrane 55, the precision of the measurements and the stability of the coupling ratio of the coupler. This is expected to be typically less than 1% full scale.

Referring now to FIG. 15, in another embodiment of the present invention a probe body 91 takes the form of a tube cut squarely at one end. A guiding member 99 is attached to and seals the square-cut end of the tube 91. A hole 912 in the side of the tube 91 is sealed by a flexible sleeve 500, the portion of the sleeve lying over the hole 912 forming a flexible membrane 55. Inside the tube 91 a plug of encapsulating silicone rubber 8 holds unfused portions 31,32 of optical fibre and together with a supporting wedge 92 forms a seal across the tube 91. A taper transition portion 3 and taper waist portion 1 are unsupported by the silicone rubber block 8 and the taper waist 1 terminates at a reflecting surface 101. Light is input to one of the unfused optical fibres 31 and propagates down the taper waist 1. Reflection from the surface 101 causes the input light to return back along the fibres 31,32 and the separate signals are monitored. Deformation of the taper waist 1 leads to splitting ratio changes. A volume 94 inside the probe body 91 is sealed from the volume outside the probe by the flexible sleeve 500, the guiding means 99 and the supporting wedge 92 and encapsulating block 8. The resilient membrane 55 deflects according to the pressure difference between the volumes and this deflection is communicated to the end of the taper waist 1 by means of a member 551 attached to the inner surface of the membrane 55 and arranged in contact with the taper waist.

In another embodiment, the input end of the fused tapered coupler comprises two input fibres and light is input to the taper waist portion down both fibres simultaneously. However, the intensities of light input down each fibre are different and distortion of the taper waist portion results in a change in an output signal from an appropriately arranged light detector, as described above.

In yet another embodiment, different wavelengths of light are input down each "input" fibre and wavelength sensitive light detectors are used. With such arrangements, splitting ratios for the respective different wavelengths can be derived, with the advantage that more information on the state of the coupler can be obtained, increasing reliability and/or accuracy or even enabling the provision of temperature compensation. FIGS. 16 and 17 show schematic plan views of two sensors embodying the present invention. These sensors are for the measurement of fluid flow velocity (e.g. in wind tunnels). The sensor of FIG. 16 comprises a rigid block or body (fixture) 800 which encapsulates portions of input and output fibres 21, 22, 31, 32. The input and output fibres are fused and tapered to form a fused tapered fibre optic coupler, the taper waist portion of the coupler being formed as a loop 11 protruding from an end surface of the fixture 800. The loop is not encapsulated by the fixture 800, and is supported by the fixture at one end only (i.e. the loop is arranged as a cantilever). The end of the loop distal the body 800 (i.e. the nominal tip of the loop) is unsupported by the encapsulating material. Hence the rigid body 800 may be attached to the surface of apparatus, leaving the loop to be deflected (bent) by fluid flowing adjacent the apparatus surface.

The sensor of FIG. 17 comprises a nominal input fibre 21 and a nominal output fibre 31, fused together and drawn down to produce a taper waist portion 1, cleaved to provide a reflecting surface 101. Unfused portions of the fibres 21, 31 are encapsulated in a rigid fixture 800, with the taper waist portion protruding from a surface of the fixture. The sensor is shown schematically with a surface of the fixture block 800 attached to a wall W of a wind tunnel, arranged such that the taper waist portion extends nominally perpendicular to the general direction of fluid flow. As fluid flow velocity increases, so does the deflection of the taper waist portion, and the coupling ratio of reflected light between the two fibres provides a measure of fluid velocity in the wind tunnel.

FIG. 18 shows a schematic perspective view of a further embodiment of the present invention. In this sensor, the encapsulating body 800 comprises an aperture (slot S), extending through it and providing a channel through which fluid can flow. The loop 11 is arranged inside the aperture. The unsupported tip of the loop inside the aperture is deflected according to the velocity of fluid flow through the aperture. This arrangement (apertured/slotted encapsulating body) provides mechanical protection for a relatively fragile sensing element (i.e. a fragile taper waist portion, in loop or single ended configuration).

Figure 19:
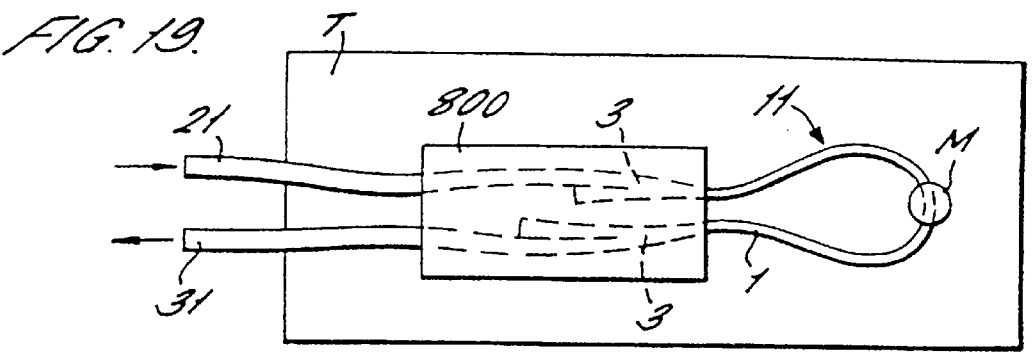
FIG. 19 is a schematic diagram of a sensor embodying the present invention, mounted on a test object, for sensing vibration/acceleration.

FIG. 19 shows a further embodiment of the present invention. The sensor of FIG. 19 is similar to that of FIG. 16, but comprises a single input fibre 21 and a single output fibre 31, protruding from a surface of a rigid encapsulating body 800. The sensor further comprises a taper waist portion of optical fibre formed by fusing together and drawing down two optical fibres. The taper waist portion is formed into a loop 11 which extends from, and so is unsupported by, the encapsulating body 800. The body 800 is shown attached to the surface T of an object O whose acceleration is to be monitored by the sensor. A mass M is attached to the looped taper waist portion and in this example is in the form of a bead of epoxy resin.

Figure 20:
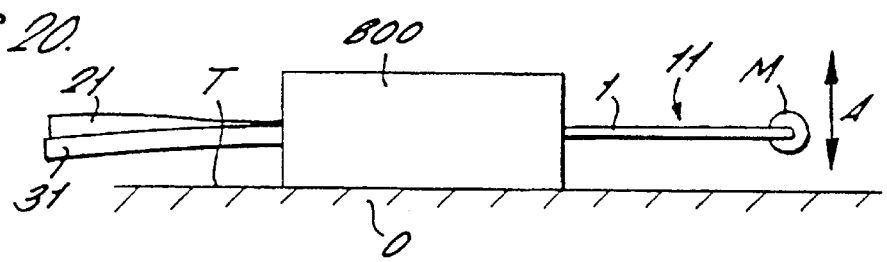
FIG. 20 is a schematic side view of the sensor of FIG. 19.

FIG. 20 shows a schematic side view of the sensor of FIG. 19. The unsupported loop 11 can be clearly seen. Acceleration of the object O having a component in the general direction shown by arrow A (i.e. perpendicular to the test surface T and plane of the loop) causes bending of the loop. The greater the mass M, the greater the bending force on the loop for a given acceleration.

The mass M can be selected/arranged to tailor the mechanical response of the taper waist portion, and so can be arranged so as to be appropriate for detecting particular frequencies of vibration. Thus, in embodiments of the present invention, adjustment of the mass attached to the taper waist portion and/or adjustment of the position of the mass relative to the point at which the taper waist portion is held by the encapsulating body, enables the frequency response of the sensor to be tailored.

Figure 21:
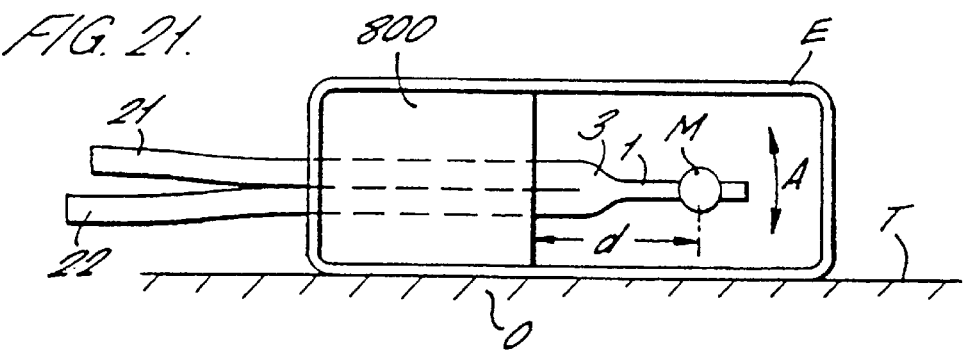
FIG. 21 is a schematic diagram of an acceleration sensor embodying the present invention.

FIG. 21 shows a further embodiment of the present invention, again a sensor suitable for measurement of vibration and/or acceleration of a test object O. In this example, the measurand responsive component is a taper waist portion of a fused tapered coupler, cleaved and mirrored to provide a reflecting surface 101. The cleaved taper waist portion extends from a surface of an encapsulating body 800 and has a mass M attached to it, at a predetermined distance d from the support point (i.e. from the body surface). The predetermined distance is selected to provide a desired response.

The end 101 of the taper waist portion 1 and mass are unsupported by the encapsulating body 800 and so the taper waist portion experiences a distorting force in response to acceleration of the body O to which the sensor is attached.

The sensor further comprises a casing (enclosure) E which protects the fragile and sensitive taper waist portion.

Thus, in embodiments of the present invention the sensor may further comprise a body (preferably rigid) encapsulating at least part of the or each unfused portion of optical fibre, the taper waist portion extending from a surface of the body such that a tip of the loop or the second end of the taper waist portion is deflectable with respect to the body to bend the taper waist portion. The taper waist portion may be arranged to bend in response to acceleration of the body or to fluid flow past the body.

A mass may be attached to the taper waist portion at a distance from the surface of the body.

A surface of the body may be adapted for attachment to apparatus, whereby in use the tip or second end is deflectable with respect to the apparatus. The body may be attached to the surface of apparatus with the taper waist portion extending into a flow of fluid past the apparatus surface.

The taper waist portion may extend from the surface of an aperture through the body, whereby the body provides mechanical protection for the taper waist portion. In use, the aperture may be arranged to permit fluid flow past the taper waist portion.

The sensor may include an enclosure fully enclosing the encapsulating body and taper waist portion, yet permitting a degree of distortion of the taper waist portion within it.

Figure 22:
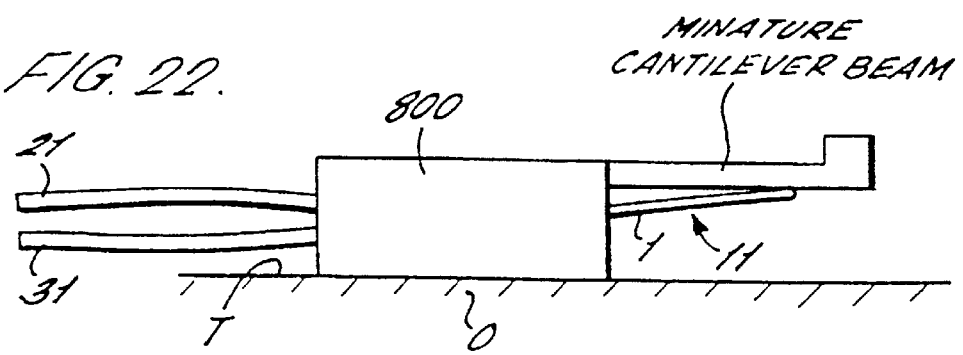
FIG. 22 is a schematic diagram of a further embodiment.

FIG. 22 shows a schematic side view of a further sensor embodying the present invention. The sensor comprises a taper waist portion of a fused tapered fibre optic coupler, formed as a loop, extending from an encapsulating fixture 800 and bonded to the nominal underside of a cantilever beam (miniature beam in this example). Input and output fibres connected to the taper waist portion extend from a further surface of the body 800. Distortion of the cantilever beam causes distortion of the loop 11, and so affects the coupling ratio between the component fibres of the fused tapered fibre optic coupler. The mechanical properties of the beam may be tailored to suit a particular application, and the optical sensor will respond to the resultant movement.

Thus the sensors of FIGS. 19 to 21 are suitable for the detection/measurement of vibration and/or acceleration, i.e. they may form part of an accelerometer. In both the fluid flow velocity sensors and acceleration/vibration sensors, the small size and passive nature of the fibre optic sensors provides clear advantages over conventional known arrangements.

Each feature disclosed in this specification (which term includes the claims) and/or shown in the drawings may be incorporated in the invention independently of other disclosed and/or illustrated features.

What is claimed is:

1. Sensing apparatus including:
   a sensor comprising
      a fused tapered fibre optic coupler formed of two optical fibres fused together to provide a fused portion which is drawn down to form a taper waist portion, the coupler having an input end comprising an input unfused portion of one of said two optical fibres and an output end comprising an output unfused portion of one of said two optical fibres;
      a light source arranged to input light to the taper waist portion along the input unfused portion; and a light detector arranged to generate a signal indicative of a parameter of the light transmitted to the output unfused portion from the taper waist portion,
   characterised in that the taper waist portion is formed as a loop and at least part of the loop is arranged to bend in response to a measurand.

2. Sensing apparatus in accordance with claim 1, wherein the sensor further comprises bending means arranged to bend at least part of said loop according to the measurand.

3. Sensing apparatus in accordance with claim 2, wherein said loop is formed substantially in a plane, and the bending means is arranged to bend the loop in said plane.

4. Sensing apparatus in accordance with claim 2, wherein said loop is formed substantially in a plane, and the bending means is arranged to bend the loop out of said plane.

5. Sensing apparatus in accordance with claim 1, wherein said loop is substantially U-shaped, incorporating a 180° bend.

6. Sensing apparatus in accordance with claim 1, wherein the input end further comprises a second input unfused portion, the second input unfused portion being an unfused portion of the other one of said two optical fibres, the input unfused portions being arranged substantially in a plane, and the loop is formed in a plane perpendicular to the plane of the input unfused portions.

7. Sensing apparatus in accordance with claim 1, wherein said input and output unfused portions are arranged substantially in a first plane, and the loop is formed substantially in said first plane.

8. Sensing apparatus in accordance with claim 1, wherein the output end further comprises a second output unfused portion, the second output unfused portion being an unfused portion of the other one of said two optical fibres, and the apparatus further includes a second light detector, the light detectors being arranged to generate respective signals indicative of a parameter of the light transmitted to each output unfused portion.

9. Sensing apparatus including:
  a sensor comprising
    a taper waist portion of optical fibre formed by fusing together and drawing down respective portions of at least two optical fibres, the taper waist portion having a first end and a second end, and
    a taper transition portion of optical fibre optically connecting the first end of the taper waist portion to at least one unfused portion of optical fibre, each unfused portion being an unfused portion of a respective one of said at least two optical fibres; and
  a light source arranged to input light to the first end of the taper waist portion along one of said at least one unfused portions,
  characterised in that the sensor further comprises
    means for reflecting at least some of the input light propagating along the taper waist portion from the first to the second end back along the taper waist portion to the first end,
  the sensing apparatus further comprises
    a light detector arranged to generate a signal indicative of a parameter of the reflected input light transmitted to one of said at least one unfused portions from the first end of the taper waist portion,
    and at least part of the taper waist portion is arranged to bend in response to a measurand.

10. Sensing apparatus in accordance with claim 9, wherein the sensor further comprises bending means arranged to bend at least part of the taper waist portion according to the measurand.

11. Sensing apparatus in accordance with claim 9, wherein the taper transition portion optically connects the first end of the taper waist portion to two said unfused portions, and the apparatus further includes a second light detector, the light detectors being arranged to generate respective signals indicative of a parameter of the reflected input light transmitted to each unfused portion.

12. Sensing apparatus in accordance with claim 9, wherein the optical fibre portions of the sensor are provided by at least part of a fused tapered coupler.

13. Sensing apparatus in accordance with claim 9, wherein the taper waist portion terminates at said second end at a substantially planar surface arranged to reflect said propagating light.

14. Sensing apparatus in accordance with claim 13, wherein said surface has been formed by cutting.

15. Sensing apparatus in accordance with claim 13 wherein said surface is mirrored.

16. Sensing apparatus in accordance with claim 10, wherein said taper waist portion is arranged to lie substantially in a plane and the bending means is arranged to bend the taper waist portion in said plane.

17. Sensing apparatus in accordance with claim 9, wherein said unfused portion or portions and said taper waist portion are substantially co-planar.

18. Sensing apparatus in accordance with claim 8, further comprising means for generating a signal indicative of the ratio of said respective signals.

19. Sensing apparatus in accordance with claim 8, further comprising means for generating a signal indicative of the ratio of the sum to the difference of said respective signals.

20. Sensing apparatus in accordance with claim 1, wherein said two optical fibres are single-mode fibres, each comprising a core surrounded by cladding material of lower refractive index, the core being dimensioned to allow only a single, fundamental mode of light to propagate down the fibre, said fundamental mode being guided by the boundary between the core and cladding material.

21. Sensing apparatus in accordance with claim 20, wherein said core has a diameter smaller than 15 µm.

22. Sensing apparatus in accordance with claim 20, wherein said taper waist portion is dimensioned such that the fundamental mode cannot substantially be guided by a boundary between cladding material and core material in the taper waist portion, but can propagate along the taper waist portion guided by an external boundary of said cladding material.

23. Sensing apparatus in accordance with claim 20, wherein said taper waist portion has a substantially uniform cross section along its length, said cross section having a diameter of less than 30 µm.

24. Sensing apparatus in accordance with claim 20, wherein said loop comprises a bend having a radius of curvature smaller than 0.5 mm.

25. Sensing apparatus in accordance with claims 24 wherein said 180° bend has a radius of curvature smaller than 0.5 mm.

26. Sensing apparatus in accordance with claim 1, wherein the taper waist portion has a substantially elliptical cross section having a major axis of symmetry.

27. Sensing apparatus in accordance with claim 1, wherein the taper waist portion has a cross section substantially resembling two overlapping circles, the cross section having a major axis of symmetry through the nominal centres of said circles.

28. Sensing apparatus in accordance with claim 1, wherein the taper waist portion has a substantially uniform cross section having at least a major axis of symmetry.

29. Sensing apparatus in accordance with claim 26, wherein said loop has been formed by bending the taper waist portion in a plane perpendicular to said major axis.

30. Sensing apparatus in accordance with claim 26 wherein said major axis is substantially parallel to said plane.

31. Sensing apparatus in accordance with claim 1, further comprising a tubular probe body, said sensor being arranged inside said body, and wherein said bending means comprises a resilient membrane, one side of at least part of the membrane being arranged to communicate with a region outside the probe body and a second side of said at least part of the membrane being arranged to communicate with a region inside the probe body, said at least part of said membrane being arranged to undergo a deflection according to a pressure difference between said regions and to communicate said deflection to the taper waist portion.

32. Sensing apparatus in accordance with claim 31 wherein an end of the probe body is obliquely terminated with respect to a longitudinal axis of the probe body, the membrane is arranged to seal said obliquely terminated end, and the sensor is arranged to hold a part of the taper waist portion in contact with the membrane.

33. Sensing apparatus in accordance with claim 31 wherein at least part of the probe body is flexible.

34. Sensing apparatus in accordance with claim 31 wherein the probe body comprises a rigid portion, at least part of at least one unfused portion of the sensor is fixed with respect to the rigid portion and the membrane seals an orifice in the rigid portion.

35. A sensor comprising a fused tapered fibre optic coupler formed of two optical fibres fused together to provide a fused portion which is drawn down to form a taper waist portion, the coupler having an input end comprising an input unfused portion of one of said two optical fibres and an output end comprising an output unfused portion of one of said two optical fibres, characterised in that the taper waist portion is formed as a loop.

36. A sensor in accordance with claim 35, further comprising bending means arranged to bend at least part of the loop according to a measurand.

37. A sensor in accordance with claim 36, further comprising a sensor body having a substantially rigid portion, wherein at least one of the input and output unfused portions is attached to the rigid portion, and the bending means is arranged to deflect the loop with respect to the rigid portion.

38. A sensor comprising a taper waist portion of optical fibre formed by fusing together and drawing down respective portions of at least two optical fibres, the taper waist portion having a first end and a second end, and a taper transition portion of optical fibre optically connecting the first end of the taper waist portion to at least one unfused portion of optical fibre, each unfused portion being an unfused portion of a respective one of said at least two optical fibres, characterised in that the sensor further comprises means for reflecting light propagating along the taper waist portion from the first to the second end back along the taper waist portion to the first end.

39. A sensor in accordance with claim 38, further comprising bending means arranged to bend at least part of the taper waist portion according to a measurand.

40. A sensor in accordance with claim 39, further comprising a body having a substantially rigid portion, wherein at least one of said at least one unfused portions is attached to the rigid portion, and the bending means is arranged to deflect the taper waist portion with respect to the rigid portion.

41. Sensing apparatus in accordance with claim 37, wherein said rigid portion is tubular and comprises an obliquely terminated end, the bending means comprises a resilient membrane sealing the obliquely terminated end and arranged to deflect according to a pressure difference across it, and at least one of the unfused portions is attached by attachment means to an inside surface of the tubular rigid portion, the attachment means being arranged to hold part of the taper waist portion in contact with the membrane.

42. A measurement method comprising the steps of:

forming a loop from a taper waist portion of a fused tapered fibre optic coupler;

inputting light to the taper waist portion along a nominal input fibre of the coupler;

generating a signal indicative of a parameter of the light transmitted to a nominal output fibre of the coupler from the taper waist portion;

distorting the loop according a measurand; and using the signal to provide an indication of the measurand.

43. A measurement method in accordance with claim 42, wherein said signal is indicative of the intensity of the light transmitted to the nominal output fibre, the method further comprising the steps of:

generating a second signal indicative of the intensity of the light transmitted to a second nominal output fibre of the coupler from the taper waist portion:

generating a further signal from said signal and said second signal, the further signal being indicative of a splitting ratio of light powers transmitted to each of said nominal output fibres; and using the further signal as an indication of the measurand.

44. A measurement method in accordance with claim 42 wherein said step of forming a loop comprises the step of forming a substantially planar loop.

45. A measurement method in accordance with claim 44, wherein said step of distorting at least part of the loop comprises bending at least part of the loop out of its nominal plane.

46. A measurement method in accordance with claim 42, wherein said step of forming a loop comprises the step of forming a u-shaped loop having a 180° bend.

47. A measurement method comprising the steps of:

inputting light to a taper waist portion of a fused tapered fibre optic coupler along a nominal input fibre of the coupler;

reflecting at least a portion of the light propagating along the taper waist portion from the input fibre back towards the input fibre;

generating a signal indicative of a parameter of the reflected light transmitted to a nominal input fibre of the coupler from the taper waist portion;

distorting at least part of the taper waist portion according to a measurand; and using the signal to provide an indication of the measurand.

48. A measurement method in accordance with claim 47, further comprising the step of cleaving the taper waist portion to provide a reflecting surface, and said step of reflecting comprises reflecting said portion of the light from said surface.

49. A measurement method in accordance with claim 47 wherein said signal is indicative of the intensity of the light transmitted to the nominal input fibre from the taper waist portion, the method further comprising the steps of:

generating a second signal indicative of the intensity of the reflected light transmitted to a second nominal input fibre of the coupler from the taper waist portion;

generating a further signal from said signal and said signal, the further signal being indicative of a splitting ratio of light powers transmitted to each of said nominal input fibres; and using the further signal as an indication of the measurand.

50. A measurement method in accordance with claim 49, wherein the nominal input fibres and the taper waist portion lie substantially in a common plane, and said distorting step comprises bending the taper waist portion in said common plane.

* * * * *